United States Patent [19]

Hemker et al.

[11] Patent Number: 5,266,462
[45] Date of Patent: Nov. 30, 1993

[54] MEASUREMENT OF PLATELET ACTIVITIES

[75] Inventors: Hendrik C. Hemker, Maastricht; Robert J. Wagenvoord, Eysden, both of Netherlands

[73] Assignee: Baxter Diagnostics Inc., Deerfield, Ill.

[21] Appl. No.: 892,865

[22] Filed: Jun. 3, 1992

[51] Int. Cl.$^5$ .......... C12Q 1/56; C12Q 1/32; G01N 33/86; A01N 37/10
[52] U.S. Cl. .......... 435/13; 435/26; 435/25; 514/570; 530/308; 530/381; 436/69; 436/63
[58] Field of Search .......... 435/13, 26, 25; 514/570; 530/308, 381; 436/69, 63

[56] References Cited

U.S. PATENT DOCUMENTS

| | | | |
|---|---|---|---|
| 4,728,660 | 3/1988 | Haynes et al. | 435/13 |
| 4,871,677 | 10/1989 | Baugh et al. | 435/13 |
| 4,880,788 | 11/1989 | Moake et al. | 514/570 |
| 4,900,679 | 2/1990 | Spillert et al. | 435/13 |
| 5,017,556 | 5/1991 | O'Brien et al. | 530/380 |
| 5,066,787 | 11/1991 | Reutelingsperger | 530/380 |
| 5,066,788 | 11/1991 | Reutelingsperger | 530/381 |
| 5,120,537 | 6/1992 | Esmon et al. | 530/381 |

OTHER PUBLICATIONS

Abstract, Proc Natl Acad Sci USA Feb. 1984, 81 (3) pp. 913-917.

*Primary Examiner*—Michael G. Wityshyn
*Assistant Examiner*—Louise N. Leary
*Attorney, Agent, or Firm*—Louise S. Pearson; Kent Barta; Cynthia G. Tymeson

[57] ABSTRACT

Methods are provided for measuring the procoagulant activity of platelets in blood by means of a chromogenic assay which is specific for procoagulant phospholipids. These methods include the determination of the resting activity and/or excitability of platelets, which determines the threshold at which activating clotting factors (circulating in blood) are dangerous. Also methods are provided for screening drugs for their potential inhibitory effect on the activation of platelets.

22 Claims, 15 Drawing Sheets

MEASUREMENT OF PLATELET ACTIVITIES

The present invention relates to methods for measuring platelet activity in blood coagulation. More specifically, the present invention relates to a chromogenic assay for determining the procoagulant activity of platelets in whole blood, to methods for determining the resting activity and/or excitability of platelets, which in turn, determines the threshold at which activating clotting factors are dangerous, and to methods for screening drugs for their potential inhibitory effect on the activation of platelets.

BACKGROUND OF THE INVENTION

Haemostasis or stoppage of blood flow can be shown to be a disturbance of a delicately poised system of two processes—coagulation and fibrinolysis. Under normal circumstances blood remains fluid, but if vascular damage occurs or if certain abnormal physiological states develop, steady states in one or both of these processes are disturbed and haemostasis results.

Blood coagulation involves more than 50 important substances which are found in the blood and tissues, some promoting coagulation ("procoagulants"), and others inhibiting coagulation ("anticoagulants"). Whether or not blood coagulates depends on the degree of balance between these two groups of substances. In the healthy individual, the anticoagulants normally predominate, and the blood remains fluid. In the stressed individual, that is those individuals with endogenously damaged vessels and especially those having certain abnormal physiological conditions, procoagulants in the affected area become "activated" and override the anticoagulants leading to the formation of thrombin which, in turn, leads to the development of a blood clot or thrombus. A thrombus is an aggregate of blood fractions, primarily platelets and fibrin with entrapment of cellular elements, frequently causing obstruction at the point of its formation.

There is general agreement that blood coagulation or clotting takes place in three essential steps. First, a complex of substances called prothrombin activator is formed, e.g., in response to rupture of the blood vessel or damage to the blood itself. Second, the prothrombin activator catalyses the conversion of prothrombin to thrombin. Third, the thrombin acts as an enzyme to activate platelets and to convert fibrinogen into fibrin threads that enmesh platelets, blood cells, and plasma to form the clot itself.

Platelets play a very important role in blood coagulation. Their role is twofold, they form aggregates and they provide procoagulant phospholipids, that is, negatively charged phospholipids. The aggregates serve as an initial plug with two functions, one which can prevent bleeding for a short period of time, and the other where they act as a sponge or niche of non-flowing plasma where thrombin can accumulate. This accumulated thrombin, in turn, activates the clotting mechanism in various ways, but importantly, it also activates platelets.

Thrombin is formed by activation of prothrombin with factor $X_a$. Factor $X_a$ is formed by activation of factor X with factor $IX_a$. Both activation reactions are slow in the absence of procoagulant phospholipids. A phospholipid membrane will only be procoagulant when a sufficient amount of negatively charged phospholipids (mostly phosphatidyl serene) are present (see, e.g., Bevers et al., *Eur. J. Biochem.* 122:429–436 (1982), the disclosure of which is hereby incorporated by reference). The outer leaflet of a resting platelet contains hardly any phosphatidyl serine. Thus, the membrane is hardly or not procoagulant. On activation of the platelet, the phosphatidyl serine present in the inner leaflet of the membrane will be exposed in the outer leaflet. This is the so-called flip-flop reaction and by this process the platelet becomes procoagulant.

Platelets can be activated not only by the natural activators thrombin and collagen, but also by calcium ionophore A23187 (Bevers, et al., supra), diamide (Van Rijn et al., *Eur. J. Biochem.* 133:1–10 (1983)) and several other compounds such as serotonin (Zucker and Nachtmias, Arteriosclerosis 5:2–18 (1985)), epinephrin, platelet activating factor, adenosine diphosphate, etc. (see Rapaport, *Introduction to haematology*:440–448). Because platelets are activated by thrombin, this compound facilitates its own formation. Besides procoagulant phospholipids, the cofactors, factors $V_a$ and $VIII_a$, are required for optimal activation of prothrombin and factor X, respectively. These cofactors are formed by activation of factors V and VIII with trace amounts of thrombin. So also in this way thrombin promotes its own formation. How the first few molecules of factors V and VIII are activated is still a matter of speculation.

As noted above, the level of activated clotting factors in whole blood usually is low because all kinds of plasma inhibitors inactivate these clotting factors. Below a certain threshold these activated factors are not harmful. Also, the amount of procoagulant phospholipids in whole blood is low because resting platelets have a mechanism to transport phosphatidyl serine from the outer to the inner leaflet of the membrane. A minor amount of the phosphatidyl serine is probably still present in the outer leaflet causing a residual procoagulant activity of the platelets. This residual or "resting activity" establishes the threshold at which activated clotting factors may result in thrombosis. Thus, the susceptibility of an individual to get thrombosis may very well be correlated with the level of procoagulant activity of his platelets.

The formation of thrombi in the human has always been a clinical condition and thus a matter of diagnosis of an illness and treatment (see Rapaport, *Introduction to Haematology*:558–576).

Previous methods for assaying the formation of thrombin are in the great majority of cases an estimation of clotting times such as the prothrombin time in any of its multiple variations. These give no information on the procoagulant activity of platelets because external phospholipids are added. The whole blood clotting time shows a very large experimental error and is dependent on haematocrit clotting factors, platelets and fibrinolysis all at the same time. Specialized laboratory tests like the thrombin generation test in platelet rich plasma are more precise, but take at least half an hour of skilled laboratory personal and are not suitable for screening a population or hospital routine.

Thus, it would be desirable to establish a method for determining the procoagulant activity of resting platelets based on the availability of negatively charged phospholipids in the outer membrane of platelets. This would facilitate the establishment of a threshold above which it could be predicted that there is a risk of thrombosis occurring. Moreover, such a test would also be useful in evaluating the susceptibility of platelets to the activating action of thrombin. It has been found, for example, that some platelets are more susceptible to the activating action of thrombin than others. This may be related to the membrane composition of the platelet, membrane fluidity or the presence of platelet inhibitors. Easily triggered platelets may result in a higher thrombosis risk, therefore warranting preventative therapeutic measures. It would also be desirable to have a method for screening drugs which, for example, inhibit the flip-flop effect of negatively charged phospholipids in the platelet's membrane. Such a test could be used to develop drugs for reducing the excitability of platelets, thus reducing the risk of thrombosis to the patient. Finally, it would be desirable for the medical/clinical practitioner to have a method for measuring the procoagulant phospholipids in whole blood, as the isolation of platelets is time consuming and not readily applicable in clinical use. Moreover, by the isolation of platelets a serious risk of platelet activation is present.

SUMMARY OF THE INVENTION

In accordance with the present invention there is provided a rapid and simple test for determining one of the three essential thrombin based feedback mechanisms of blood coagulation, namely, the generation of platelet procoagulant activity. The test is based on the amount of procoagulant phospholipids which are exposed at the outer membrane of platelets. The amount of procoagulant phospholipids present at the outer membrane interface can be used to develop tests for determining the resting activity of platelets, the excitability of platelets, as well as the procoagulant activity of platelets in whole blood. The flip-flop reaction of procoagulant phospholipids together with the ability to determine the presence of procoagulant phospholipids in the outer membrane also provides the basis for evaluating drugs which, for example, inhibit the flip-flop reaction.

More specifically, there is provided an assay which measures the amount of procoagulant phospholipids in isolated platelets, platelet rich plasma or whole blood. In one embodiment, a blood sample or platelet rich plasma is diluted with for example, saline. The diluted sample is mixed with a substrate which can be activated by an enzyme(-complex) that is procoagulant phospholipid dependent, such as prothrombin. Then by addition of the enzyme, coenzyme and required cations, such as factor $X_a$, factor $V_a$, and $CaCl_2$ a reaction system is created in which the activation reaction, e.g. prothrombin activation, is linearly dependent on the amount of procoagulant phospholipids in the blood or plasma.

In another embodiment, a variation of the above assay can be used to establish the resting activity and/or excitability of platelets. The resting activity and/or excitability of platelets can be used to determine those who are thrombosis risks. Similarly, by a modification of the above method, an assay can be used to screen for drugs which reduce the excitability of platelets and/or reduce the presence of procoagulant phospholipids to a level below the threshold where such activity results in the series of events which lead to thrombosis.

DETAILED DESCRIPTION OF THE INVENTION

Figure 1:
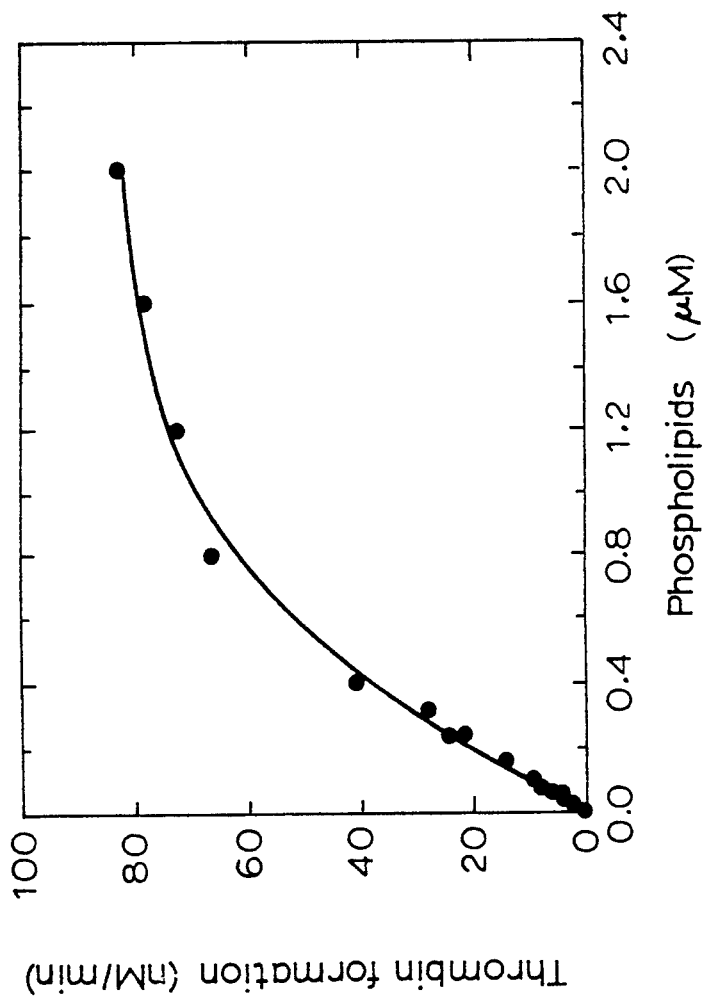
FIG. 1 shows the rate of thrombin formation as a function of the concentration of procoagulant phospholipids.

Measurement of Small Concentrations in Procoagulant Phospholipids.

The first step in developing the assays in accordance with the present invention is to establish a test which measures small amounts of negatively charged phospholipids. In order to accurately measure the activity of such procoagulant phospholipids, it is preferable to have an assay which is linearly dependent on the concentration of the procoagulant phospholipids and capable of detecting small amounts of phospholipids. To measure the amount of negatively charged phospholipids, an enzymatic reaction is required that is dependent on such phospholipids. Examples of such reactions are the complete factor X activating complex and the complete prothrombinase. Other reaction systems which can also be used include incomplete factor X and prothrombin activating mixtures (lacking factor $VIII_a$ and factor $V_a$, respectively). For optimal action of the factor X activating complex, factor $IX_a$ and factor $VIII_a$ are required, whereas for the complete prothrombinase, factor $X_a$ and factor $V_a$ are required. Since factor $VIII_a$ has been observed to be unstable in plasma, for reasons as yet unknown, it is preferred to employ the components of the complete prothrombinase.

The assay for measuring small amounts of procoagulant phospholipids can be carried out as follows:

Two mixtures are prepared, reagent A and reagent B. Reagent A contains, for example, factor $V_a$, factor $X_a$ and $CaCl_2$, while reagent B contains prothrombin. One preferred approach for conducting the assay is to add phospholipids to reagent A, thus providing all the components of the complete prothrombinase, and then measure the prothrombinase activity by addition of prothrombin and a suitable chromogenic substrate. The amount of factor $V_a$, which can be used is generally between 0.2 and 8 nM, more preferably between 0.6 and 3 nM. For factor $X_a$ these numbers are about the same, however, the ratio between factor $V_a$ and $X_a$ should be between 1 and 2. The amount of $CaCl_2$, which can be used is generally between 2 and 40 mM, more preferably between 4 and 8 mM. The amount of prothrombin, which can be used is generally between 0.6 and 24 $\mu M$, more preferably between 2 and 12 $\mu M$.

Table I illustrates results of one approach where:

i) reagent A is prepared with 240 pM factor $X_a$ and 15 mM $CaCl_2$;

ii) reagent B contains 6 $\mu M$ prothrombin;

iii) the stock phospholipid concentration is 3 mM (75 mole-% phosphatidyl choline and 25 mole-% phosphatidyl serine) diluted to the concentrations illustrated in Table 1; and iv) the pipetting scheme is 100 $\mu l$ reagent A mixed with 100 $\mu l$ phospholipids followed by incubation at 37° C. for 5 minutes, whereafter 100 $\mu l$ reagent B is added. Samples of 100 $\mu l$ are taken after 2 and 4 minutes reaction time to measure formed thrombin using a stop buffer (880 $\mu l$ of 10 mM EDTA), a chromogenic substrate and an optical analyzer such as any spectrophotometer capable of measuring accurately at 405 nm or 396 nm.

FIG. 1 shows that the rate of thrombin formation is linear with the phospholipid concentration up to about 0.4 $\mu M$ in the reaction mixture, which means that phospholipids up to 1.2 $\mu M$ in the sample can be measured accurately. To measure higher phospholipid concentration, either the sample should be diluted, or a smaller sample, for example 20 $\mu l$, should be added, thus reducing the amount of phospholipids.

The amount of formed thrombin is proportional with the hydrolysis rate (m$\Delta$A/min) of the chromogenic substrate, in this case S2238. The proportionality number depends on the substrate, the concentration of the substrate and the pH and the salt strength of the used buffer.

TABLE I

| Phospholipid ($\mu M$) | Hydrolysis rates (m$\Delta$A/min) at 2 min | | at 4 min | | Thrombin formation (nM/min) |
|---|---|---|---|---|---|
| 0 | 0.05 | | 0.28 | | 0.003 |
| 60 | 1588.0 | 1569.4 | 2661.2 | 2322.4 | 90.01 |
| 1.2 | 894.9 | 891.2 | 1622.4 | 1602.0 | 50.92 |
| 2.4 | 1181.6 | 1151.0 | 2116.3 | 2076.0 | 66.49 |
| 3.6 | 1289.8 | 1250.0 | 2091.8 | 2236.0 | 72.40 |
| 4.8 | 1375.5 | 1379.6 | 2200.0 | 2173.5 | 78.54 |
| 6.0 | 1471.4 | 1458.0 | 2216.0 | 2259.2 | 83.51 |
| 0.24 | 142.48 | 128.09 | 256.52 | 230.47 | 7.71 |
| 0.48 | 259.94 | 242.61 | 467.32 | 440.30 | 14.33 |
| 0.72 | 330.50 | 425.04 | 617.96 | 801.98 | 21.54 |
| 0 | 0.42 | 0.61 | 0.79 | 0.78 | 0.03 |
| 0.06 | 38.26 | 34.30 | 68.00 | 60.64 | 2.07 |
| 0.12 | 69.48 | 71.06 | 121.32 | 127.72 | 4.01 |
| 0.18 | 157.42 | 103.26 | 292.50 | 185.60 | 5.89 |
| 0.24 | 143.14 | 146.18 | 259.36 | 189.60 | 8.25 |
| 0.30 | 149.14 | 171.48 | 271.22 | 373.48 | 9.14 |

The activity of the complete prothrombinase complex as a function of the phospholipid concentration. To calculate the rate of thrombin formation only the 2 mini-samples were used.

By working at a constant salt strength and pH, and using a fixed substrate concentration, this number is a constant. In this particular case the number is 0.0114.

It has also been demonstrated that increasing the concentrations of factor $V_a$ and/or factor $X_a$ increases the amount of formed thrombin (see Table II). Specifically, reagent A was prepared with 0.24 nM, 0.48 nM, 0.72 nM, 0.96 nM and 1.2 nM of factors $X_a$ and $V_a$; then phospholipids of 1 $\mu M$ (FIG. 2A) and phospholipids of 0.1 $\mu M$ (FIG. 2B) were measured.

Table II shows that under the described conditions the rate of thrombin formation is dependent on the enzyme-complex concentration and this concentration should preferably be kept constant in order to have a reaction system in which prothrombin activation is dependent only on the added amount of procoagulant phospholipids. An enzyme-complex concentration between 0.2 and 4.0 nM, preferably of about 1.2 nM should be used to obtain a signal as high as possible. This is important, particularly where it is desired to measure accurately the procoagulant phospholipid concentration in whole blood, which usually is low.

TABLE II

| Factors $X_a$ and $V_a$ (pM) | | Hydrolysis rates (m$\Delta$A/min) at 2 min | | at 4 min | | Thrombin formation (nM/min) |
|---|---|---|---|---|---|---|
| A | 240 | 174.90 | 179.14 | 343.14 | 318.52 | 19.52 |
| | 480 | 525.57 | 547.44 | 967.31 | 1013.09 | 58.81 |
| | 720 | 973.65 | 996.14 | 1883.7 | 1867.3 | 109.61 |
| | 960 | 1342.0 | 1349.4 | — | — | 153.44 |
| | 1200 | 1677.6 | 1765.3 | — | — | 196.29 |
| B | 240 | 26.34 | 27.58 | 48.36 | 51.93 | 2.97 |
| | 480 | 84.81 | 87.30 | 165.64 | 178.31 | 9.81 |
| | 720 | 148.01 | 146.61 | 325.00 | 313.23 | 17.50 |
| | 960 | 223.83 | 227.98 | 482.01 | 481.87 | 26.62 |
| | 1200 | 264.98 | 272.30 | 562.30 | 589.36 | 31.73 |

Phospholipid determination with prothrombinases, which contained variable amounts of factors $X_a$ and $V_a$. A, the phospholipid concentration is 1 $\mu M$; B, the phospholipid concentration is 0.1 $\mu M$.

Figure 2B:
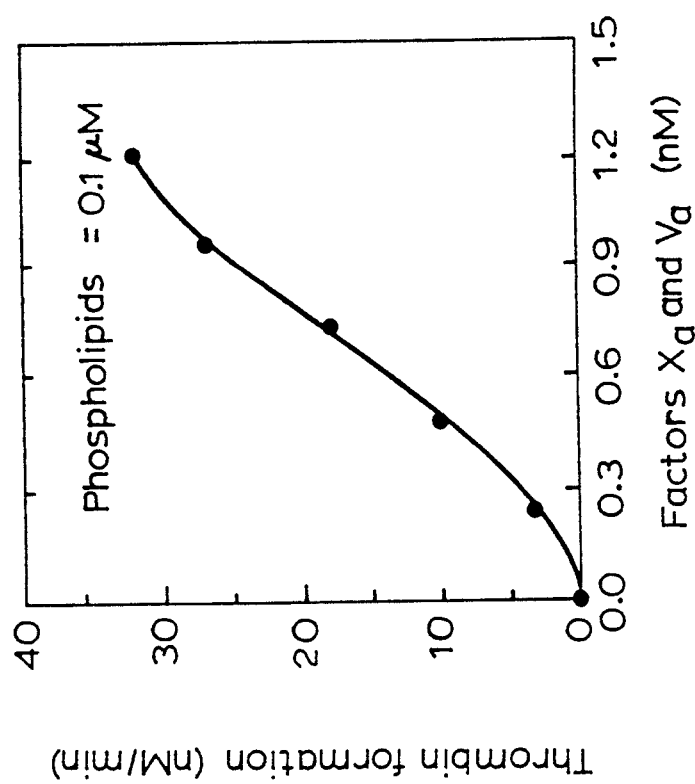
FIGS. 2A and 2B show the effect of increased concentration of factors $X_a$ and $V_a$ on thrombin formation at 1.0 $\mu$M and 0.1 $\mu$M procoagulant phospholipid concentration, respectively.
Figure 2A:
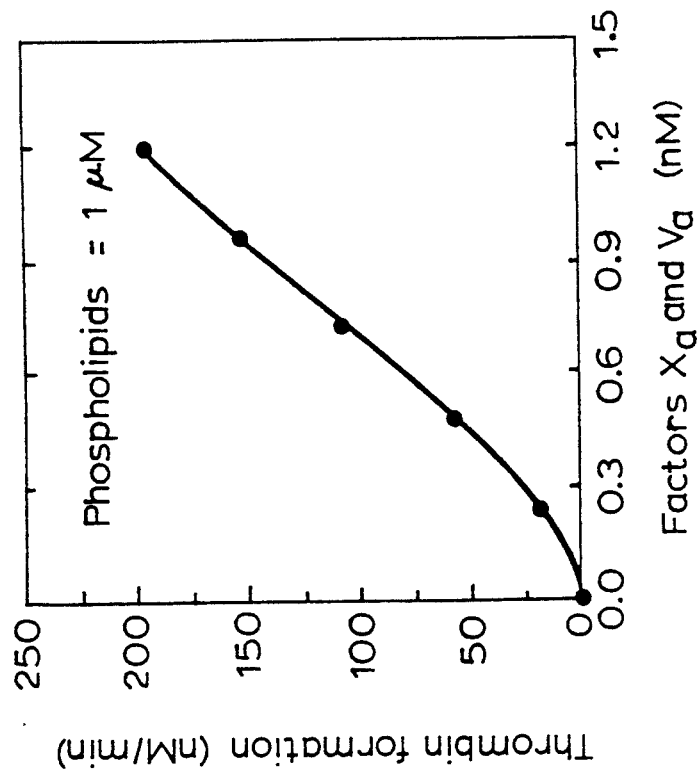

The results of Table 11 are plotted in FIG. 2. One can conclude that by increasing the concentration of factors $X_a$ and $V_a$ from 0.24 to 1.2 mM (see FIG. 2) the rate of thrombin formation increases about 10 fold, as can be expected because at low enzyme(-complex) concentration the reaction rate is linearly dependent on the enzyme(-complex) concentration. FIG. 2 shows that at concentrations above 1 nM the rate of thrombin formation is levelling off. This effect is shown with both 1 μM (FIG. 2A) and 0.1 μM (FIG. 2B) phospholipids, which probably means that at these concentrations all phospholipids are bound in the prothrombinase complex, or that other processes become rate limiting (diffusion). FIG. 2 shows that phospholipid concentrations as low as 0.01 μM can be measured.

Measurement of Procoagulant Phospholipids in Platelets

In order to develop an assay for determining the resting activity and/or excitability of platelets, it can be demonstrated that the described method works on isolated platelets. The procoagulant activity of isolated platelets may be expressed as the equivalent molar amount of procoagulant phospholipids as these negatively charged phospholipids are responsible for the procoagulant activity of platelets.

Platelets may be isolated from subject/patient blood by gel filtration (see Lages et al., *J. Lab. Clin. Med.* 85:811–825 (1975)), or centrifugation (see Bevers et al., *Biochim. Biophys. Acta* 736:57–66 (1983)). The concentration (cells/ml) is determined by measuring their absorption at 405 nm. Once the platelets have been isolated, the procoagulant activity can be measured according to the method described above for measuring small concentrations of phospholipids.

a) The Effect of Platelet Concentration

The procoagulant activity of platelets as a function of their concentration can be measured as follows: Two reagents are prepared: A and B. Reagent A contains 240 pM factor $V_a$, 240 pM factor $X_a$ and 15 mM $CaCl_2$. Reagent B contained 6 μM prothrombin. In this experiment the platelet concentration is $3.44 \times 10^8$ cells/ml.

The pipetting scheme is: 300 μl reagent B is mixed with 300 μl diluted platelets. After 5 minutes preincubation at 37° C. 300 μl reagent A is added. Samples of 100 μl are taken after 0.5, 1, 1.5, 2, 2.5, 3, 3.5 and 4 min. reaction time to measure formed thrombin. In the cuvettes are pipetted 880 μl stopbuffer (10 mM EDTA), the 100 μl sample and to measure formed thrombin 20 μl S2238 (a chromogenic substrate form AB Kabi Diagnostics, Stockholm, Sweden). In Table Ill the effect of the platelet concentration on thrombin formation is shown. As a control, the activity is given with 1 /AM phospholipids (25 mole-% phosphatidyl serine, 75 mole-% phosphatidyl choline) in the added sample, the found hydrolysis rates are 375.63 and 785.67 mΔA/min after 1 and 2 min. reaction time, respectively.

Figure 3B:
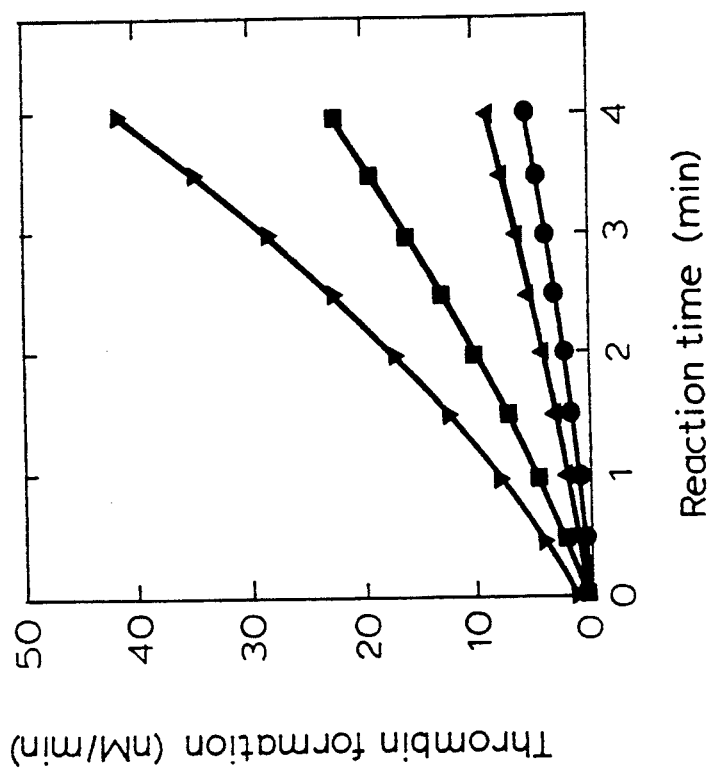
FIG. 3A shows the effect of platelet concentration on thrombin formation in a reaction mixture with factor $X_a$, factor $V_a$, $CaCl_2$ and prothrombin. See the text for he methods. The platelets ($3.55 \times 10^8$ cells/ml) were diluted 10 times (-o-), 5 times (-$\Delta$-), diluted 2 times (-$\square$-) and not diluted (-$\nabla$-). The curves were simulated with the formula $y = ax^3 + bx^2 + cx + d$, in which y is the formed thrombin and x the reaction time. The derivatives of the equations were plotted in FIG. 3B.
Figure 3A:
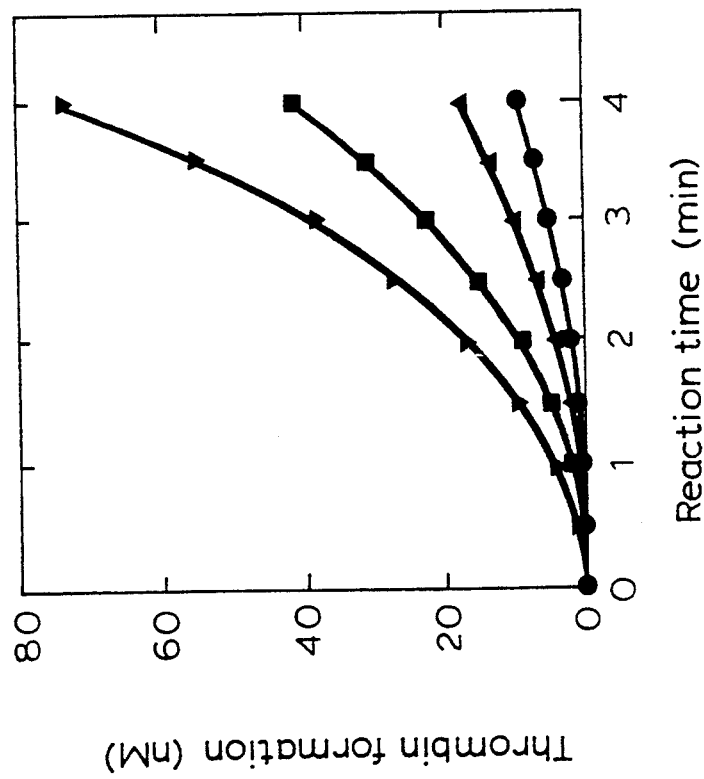

FIG. 3 shows the effect of platelet concentration on the rate of thrombin formation. FIG. 3A shows found data. The line is drawn, assuming that the amount of formed thrombin is a third order equation. The derivative (the rate of thrombin formation at each time point) is plotted in FIG. 3A. One observes that the rate of thrombin formation increases in time and that the shape of the curves is the same for every dilution. The rate of thrombin formation, which is a measure for the procoagulant activity of the platelets, is proportional to the platelets concentration. This indicates that one has to work at constant platelet concentration (or to correct for it) to measure the procoagulant activity per platelet.

TABLE III

| Sub-sample time (min.) | Hydrolysis rates (mΔA/min) | | | | |
|---|---|---|---|---|---|
| | Platelet dilution | | | | Sonicate |
| | 10 × | 5 × | 2 × | 1 × | 10 × |
| 0.5 | 1.03 | 2.23 | 4.99 | 9.55 | 239.25 |
| 1 | 3.57 | 8.44 | 18.25 | 32.93 | 687.80 |
| 1.5 | 9.23 | 18.18 | 42.56 | 77.77 | 1181.45 |
| 2 | 17.15 | 35.34 | 72.87 | 145.63 | 1678.52 |
| 2.5 | 28.53 | 57.89 | 131.87 | 234.34 | 2174 |
| 3 | 42.41 | 82.71 | 195.00 | 328.49 | 2594 |
| 3.5 | 58.49 | 112.98 | 267.11 | 478.29 | 2952 |
| 4 | 82.04 | 150.43 | 361.38 | 641.84 | 2980 |

The effect of the platelet concentration on the rate of thrombin formation, which is a measure for the procoagulant activity of the platelets and the effect of sonication of the platelets on the rate of thrombin formation is shown.

For this reason the measured procoagulant activity should be corrected for the platelet count (amount of platelets), which can be measured in different ways.

i) The optical density of at 405 nm of isolated platelets is measured, which is proportional with the platelet concentration.

ii) Platelets are counted in a platelet counter. Both isolated platelets and platelets in whole blood can be counted.

iii) Platelets can be activated completely by treatment with calcium ionophore A23187, which causes complete randomization of the phospholipids (thus also of the phosphatidyl serine) over both membranes. Because the phospholipid composition is virtually a constant, the reached procoagulant activity will be dependent on the amount of platelets only.

b) Sonication of the Platelets

Figure 4B:
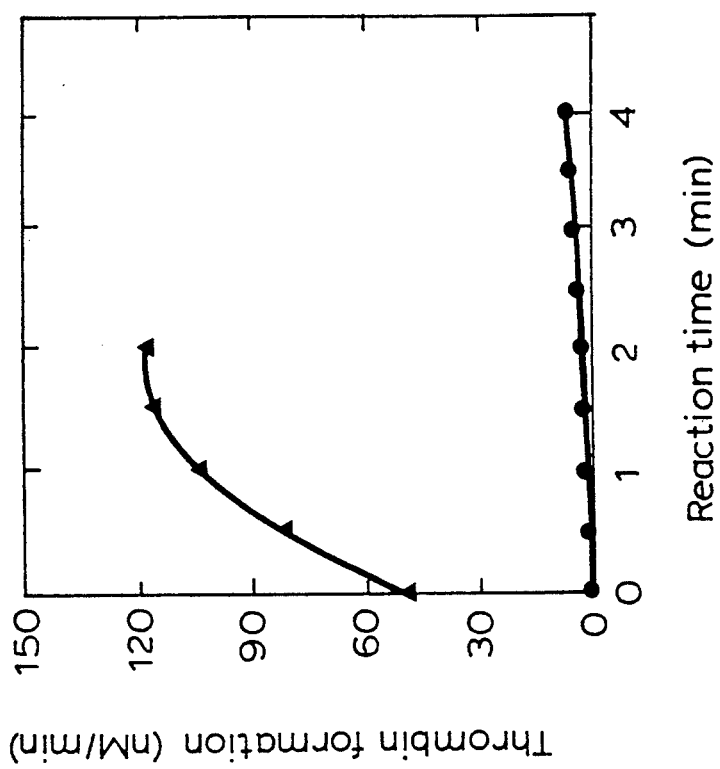
FIG. 4B is the derivative of FIG. 4A.
Figure 4A:
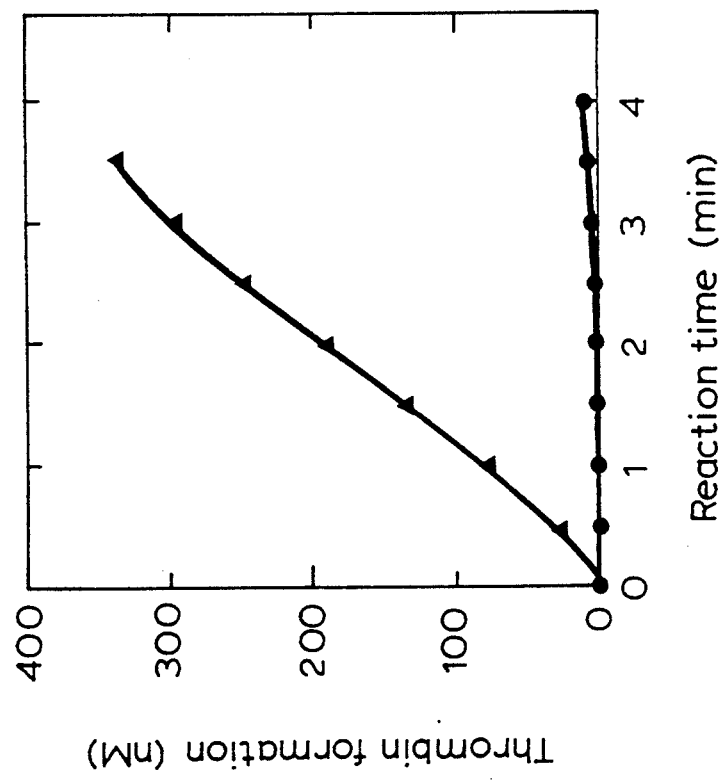
FIG. 4A shows the effect of sonication on the procoagulant activity of platelets. Platelets ($3.44 \times 10^7$ cells/ml) were sonicated during 5 minutes at 6 $\mu$ peak to peak. 300 $\mu$l of non-treated (-o-) platelets ($3.44 \times 10^7$ cells/ml) or the sonicated platelets (-$\Delta$-) were tested as in FIG. 3A.

In Table Ill and FIG. 4 the effect of sonication of the platelets on the procoagulant activity is shown. As can be seen, an enormous increase in activity is found, indicating that the test system is a good tool to measure even very high procoagulant activities, and confirming earlier found data.

c) Effect of Thrombin on the Platelets

The procoagulant activity of the platelets is measured as before with the same reagents as above. In this case, however, the platelets are preincubated with thrombin. In Table IV the effect of pretreatment of platelets with thrombin and thrombin plus $CaCl_2$ is shown.

Figure 5B:
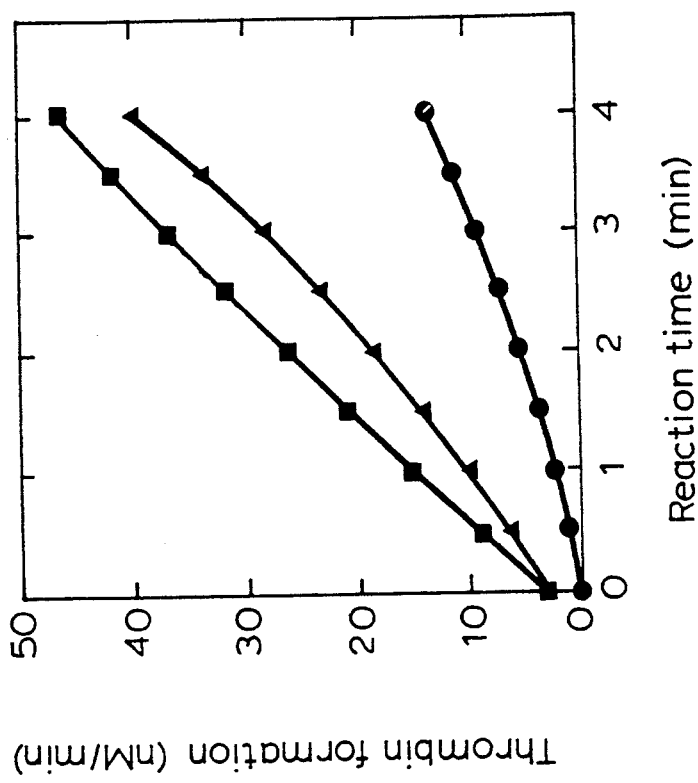
FIG. 5B is the derivative of FIG. 5A.
Figure 5A:
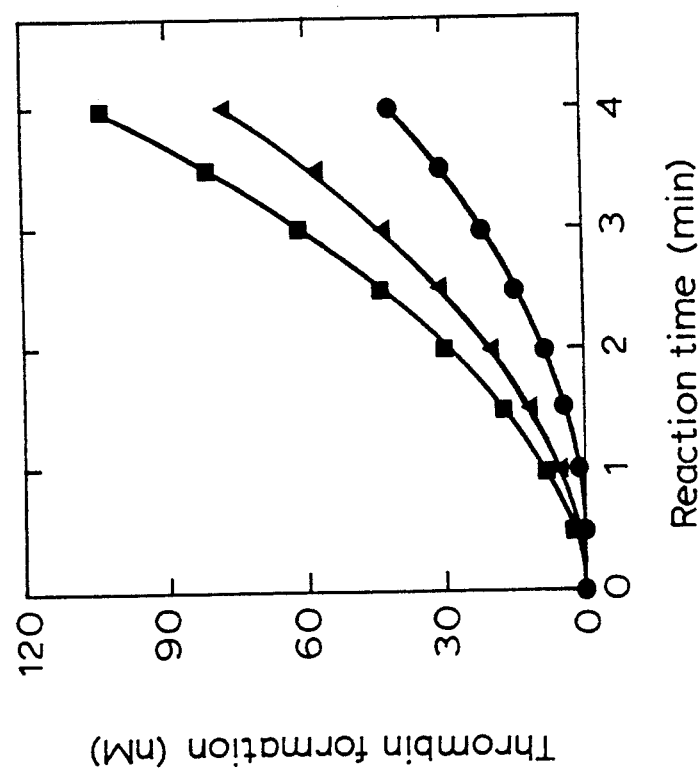
FIG. 5A shows the effect of thrombin and thrombin plus $CaCl_2$ on procoagulant activity of platelets. Platelets ($1.72 \times 10^8$ cells/ml) were not treated (-o-), incubated with 3.3 nM thrombin or with 3.3 nM thrombin, 2 mM $CaCl_2$ (-$\square$-). The further procedure is described in FIG. 1.
Figure 6B:
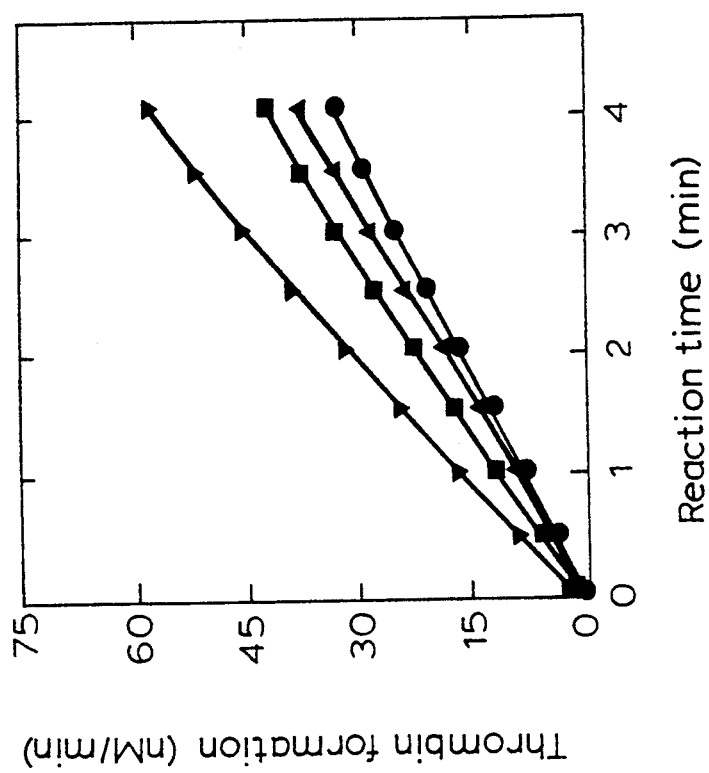
FIG. 6A shows the effect of thrombin, collagen and thrombin plus collagen on procoagulant activity of platelets. Platelets ($1.62 \times 10^8$ cells/ml) were not treated (-o-), incubated with 4.0 nM thrombin (-$\Delta$-) with 1 $\mu$g/ml collagen (-$\square$-) or with 4.0 nM thrombin plus 1 $\mu$g/ml collagen (-$\nabla$-). The further procedure is earlier described. The lines are third order simulations. The derivative of the lines in FIG. 6A are given in FIG. 6B.
Figure 6A:
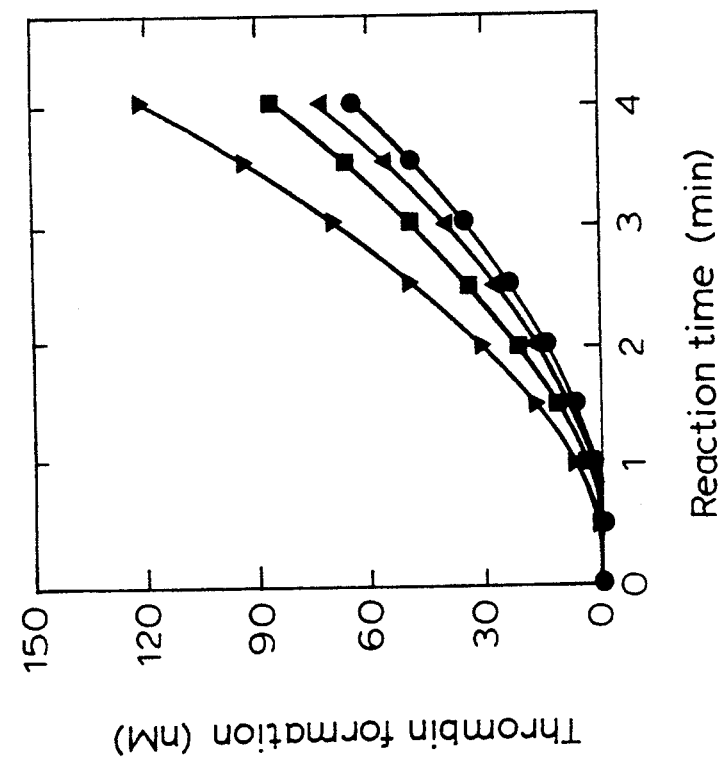

FIG. 5 shows that pretreatment of the platelets with 3.3 nM thrombin has a stimulating effect on thrombin formation. When thrombin (3.3 nM) plus $CaCl_2$ (1 mill) is present this stimulating effect is somewhat larger.

TABLE IV

| Sub-sample time (min.) | Hydrolysis rates (mΔA/min) | | |
|---|---|---|---|
| | Control | $FII_a$ | $FII_a$ + Ca |
| 0.5 | 4.99 | 20.76 | 30.46 |
| 1 | 18.25 | 51.86 | 77.51 |
| 1.5 | 42.56 | 101.81 | 157.40 |
| 2 | 72.87 | 178.02 | 266.06 |
| 2.5 | 131.87 | 273.06 | 389.68 |
| 3 | 195.00 | 379.36 | 540.07 |
| 3.5 | 267.11 | 502.66 | 712.04 |
| 4 | 361.38 | 678.69 | 905.88 |

The effect thrombin and thrombin plus CaCl2 on the procoagulant activity of platelets. Platelets were treated as indicated in FIG. 5.

This result confirms earlier found data, so the developed assay-system is a good tool to measure the susceptibility of platelets to thrombin induced activation.

d) Effect of Thrombin plus Collagen on Platelets

In this experiment the effect of thrombin plus collagen on the procoagulant activity of platelets is studied. This activity is measured in the same way as described above. As a control 1 μM phospholipids are tested in the assay system. The found hydrolysis rates were 390.96 and 741.71 mΔA/min after respectively 1 and 2 min. reaction time. The platelet concentration is $1.62 \times 10^8$ cells/ml.

In Table V the procoagulant activity of platelets during the prothrombinase assay by sub-sampling in time and following the rate of thrombin formation was followed. In Table V two experiments are shown: i) the effect of sonication of the platelets on the thrombin formation; and ii) the effect of pretreatment of platelets with thrombin, collagen and thrombin plus collagen.

TABLE V

| Sub-sample time (min.) | Hydrolysis rates (mΔA/min) | | | | |
|---|---|---|---|---|---|
| | Control | Sonicate | $FII_a$ | Collagen | $FII_a$ + collagen |
| 0.5 | 4.76 | 21.72 | 19.85 | 10.60 | 26.52 |
| 1 | 24.26 | 73.71 | 46.38 | 45.46 | 79.44 |
| 1.5 | 69.64 | 151.53 | 95.27 | 103.58 | 169.43 |
| 2 | 130.59 | 214.68 | 164.61 | 191.65 | 287.79 |
| 2.5 | 214.57 | 296.61 | 261.39 | 305.19 | 453.36 |
| 3 | 316.40 | 376.92 | 369.44 | 436.69 | 623.82 |
| 3.5 | 437.35 | 461.28 | 508.72 | 583.17 | 836.69 |
| 4 | 570.36 | 532.73 | 662.43 | 763.81 | 1082.69 |

The effect of sonication (platelets are 10×diluted), thrombin, collagen and thrombin plus collagen on the procoagulant activity of platelets. A control is also shown.

These experiments confirm earlier findings and thus show that the assay-system that is developed, is a good tool to measure procoagulant activity of platelets.

e) Incubation of Platelets with Thrombin in Time

In this experiment the effect of treatment of platelets with thrombin in time is studied. The test-system is earlier described. As a control, 1 μM phospholipids were tested, giving hydrolysis rates of 281.86 and 547.38 mΔA/min after respectively 1 and 2 min. The stock platelet concentration was $1 \times 10^8$ cells/ml.

In this experiment platelets were incubated with 4 nM thrombin in time and their procoagulant activity was measured after 15, 60 and 180 minutes incubation. In Table VI the results are shown.

Figure 7:
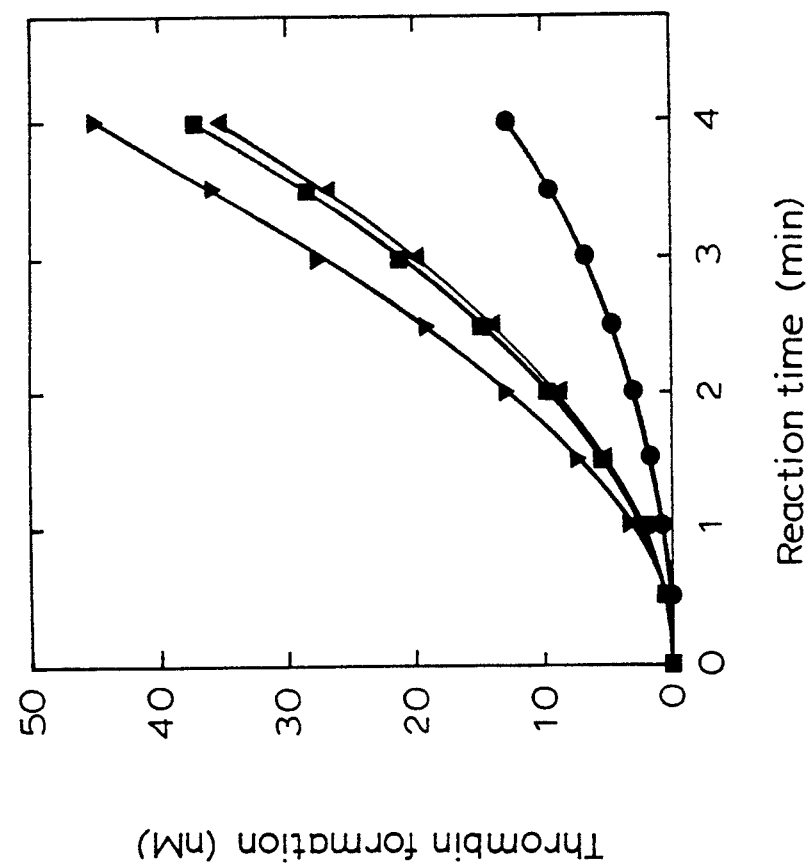
FIG. 7, shows the effect of thrombin incubation in time on the procoagulant activity of platelets. Platelets ($1 \times 10^8$ cells/ml) were not treated (-o-), or incubated with 4 nM thrombin during 15 (-$\Delta$-), 60 (-$\square$-) and 180 minutes (-$\nabla$-).

The results are plotted in FIG. 7. One can notice that platelets, which are incubated with 4 nM thrombin during 15 minutes, expose more procoagulant phospholipids than control platelets. The procoagulant activity of platelets slowly increases after the first 15 minutes incubation times. This increase of procoagulant activity after the first 15 minutes is not due to the effect of thrombin, but to aging of the platelets.

This shows that the test should be preferably carried on a fresh sample if maximal discrimination is to be obtained.

TABLE VI

| Sub-sample time (min.) | Hydrolysis rates (mΔA/min) | | | |
|---|---|---|---|---|
| | Control | $FII_a$-15 | $FII_a$-60 | $FII_a$-180 |
| 0.5 | 2.51 | 15.59 | 15.68 | 17.19 |
| 1 | 6.86 | 29.54 | 30.61 | 39.57 |
| 1.5 | 15.02 | 59.59 | 58.99 | 75.57 |
| 2 | 25.46 | 90.21 | 96.38 | 123.60 |
| 2.5 | 40.37 | 135.65 | 142.27 | 179.43 |
| 3 | 59.94 | 188.03 | 197.58 | 254.38 |
| 3.5 | 82.93 | 248.90 | 261.63 | 326.17 |
| 4 | 112.46 | 324.09 | 339.51 | 407.44 |

Procoagulant activity of platelets after treatment with 4 nM thrombin during 15, 60 and 180 minutes.

f) Effect of the Calcium ionophore A23187 on Platelets

In this experiment platelets are treated with 1 μM A23187 (see Pressman, Ann. Rev. Biochem. 45:501-530 (1976) for review on ionophores and structure formula of A23187; the reagent was obtained from CalBiochem-Hoechst, USA) and subsequently the procoagulant activity is measured. A comparison was made with a sonicate and control platelets. The earlier described method to test the procoagulant activity of platelets is used. The platelet concentration is $1.5 \times 10^8$ cells/Ml.

Figure 8B:
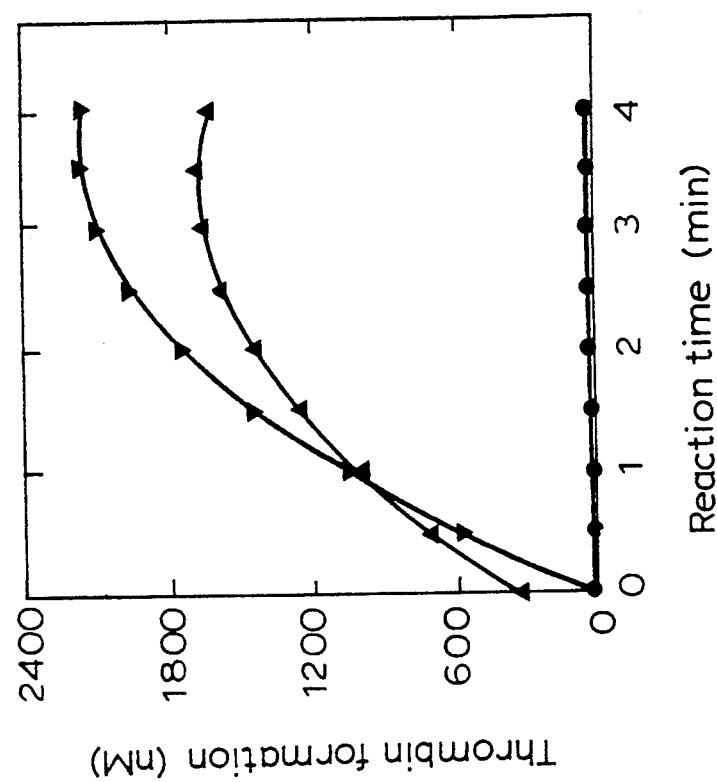
FIG. 8B gives the derivative of FIG. 8A.
Figure 8A:
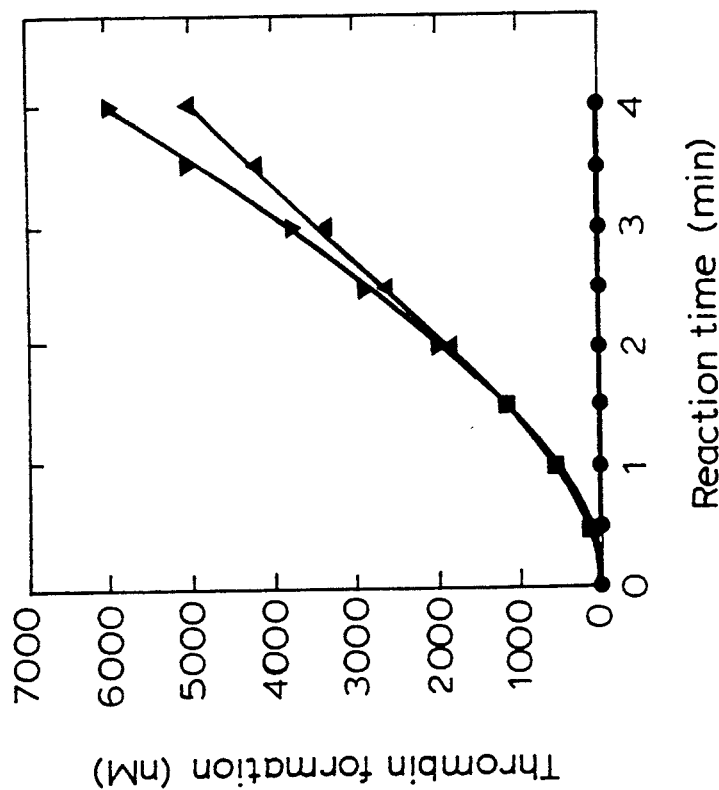
FIG. 8A shows the effects of sonication, or treatment with calcium ionophore A23187 on procoagulant activity of platelets. Platelets ($1.5 \times 10^8$ cells/ml) were not treated (-o-), or platelets ($3 \times 10^6$) were sonicated during 5 min. at 6 $\mu$ peak to peak (-$\Delta$-), or incubated with 1 $\mu$M calcium ionophore A23187 during 5 min. (-$\nabla$-). The found rates of thrombin formation in cases of the sonicate and the ionophore treatment were multiplied by 50.
Figure 10:
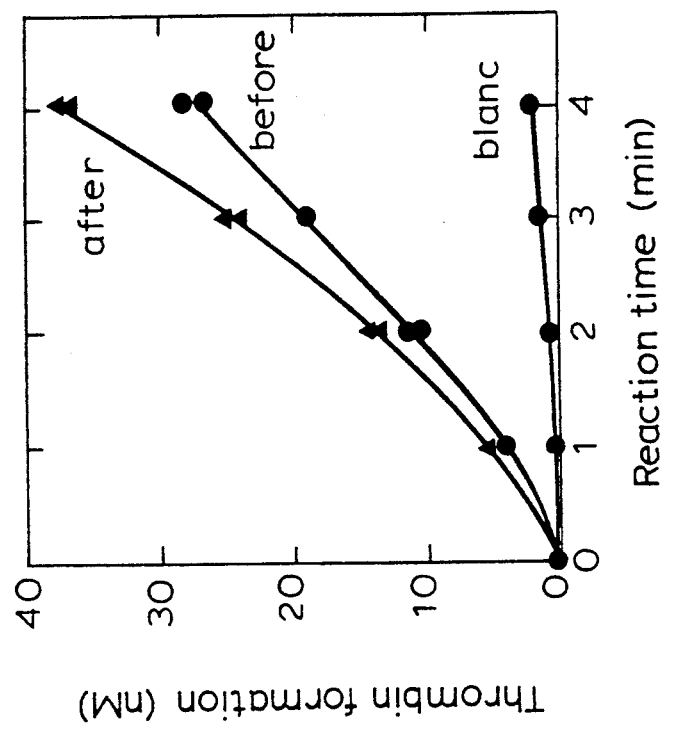
FIGS. 9-16 show measurement of the procoagulant activity of whole blood before and after physical effort of healthy volunteers.
Figure 9:
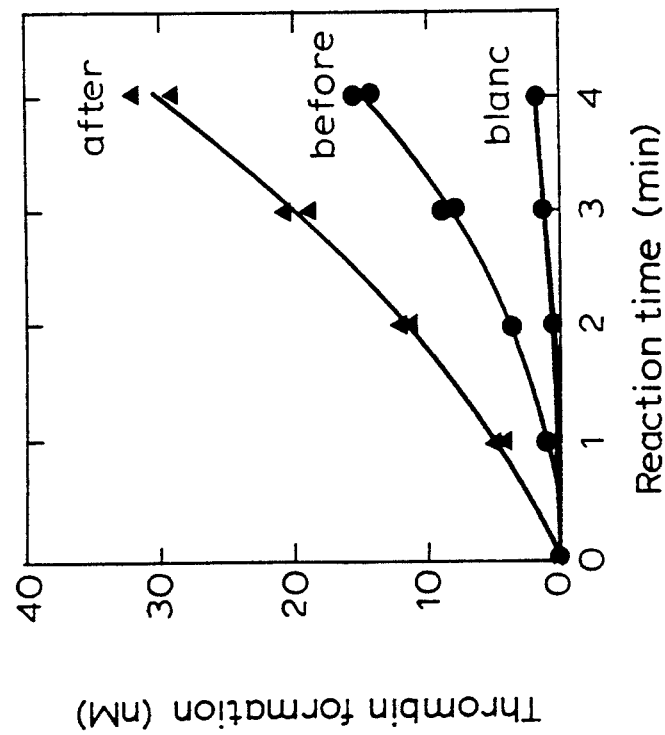
Figure 12:
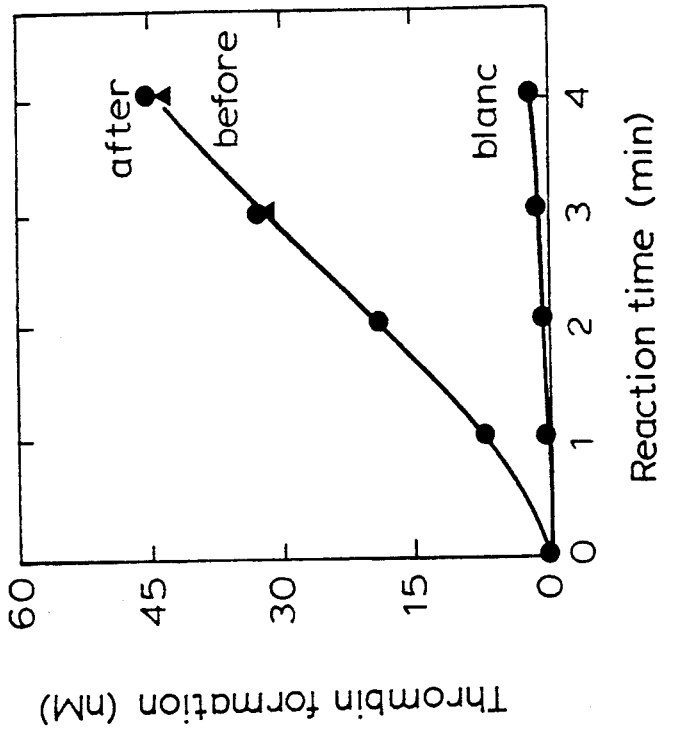
Figure 11:
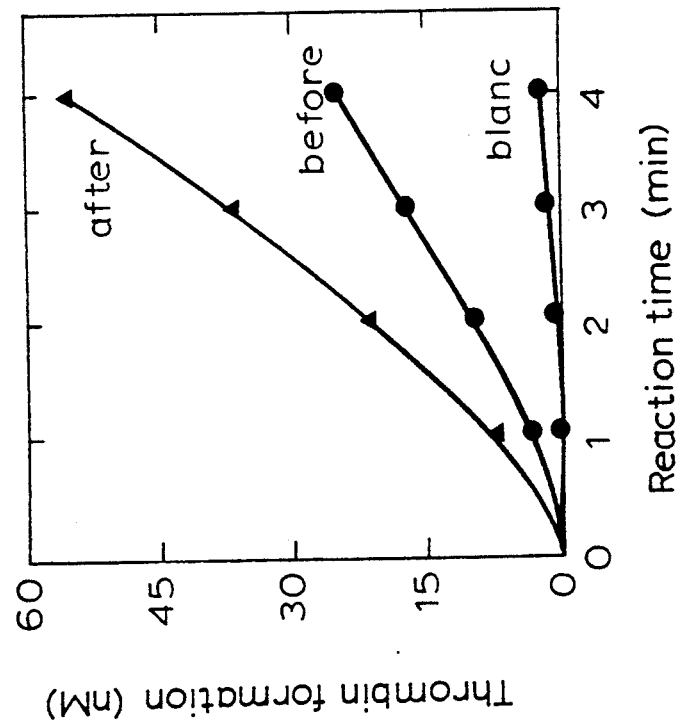
Figure 14:
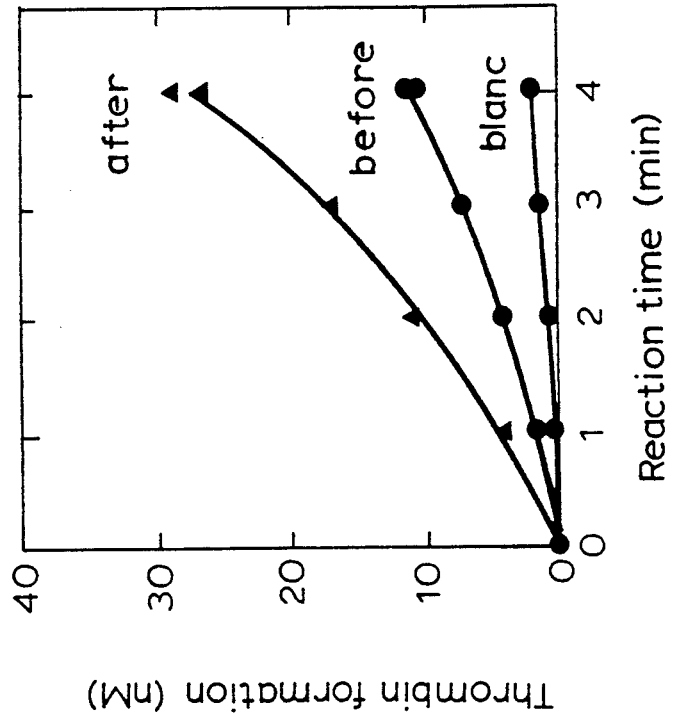
Figure 13:
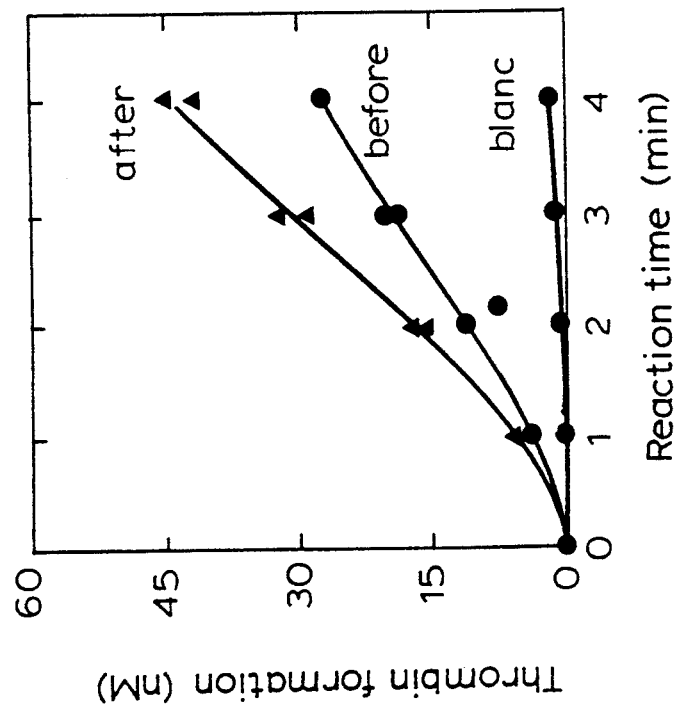
Figure 16:
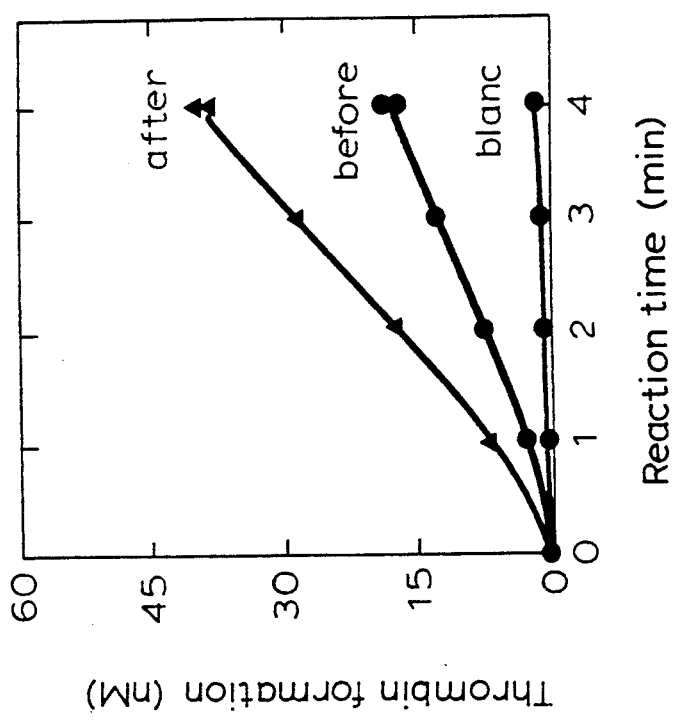
Figure 15:
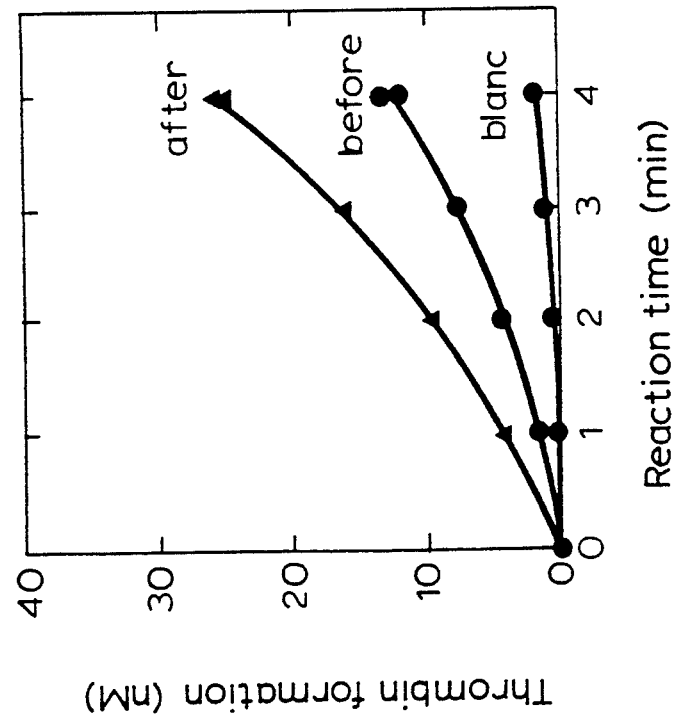

In Table VII and FIG. 8 the effect of sonication of the platelets, the effect of pretreatment of platelets with the calcium ionophore A23187 (1 μM) and a control are shown. Both treatments cause an enormous increase of procoagulant activity.

TABLE VII

| Sub-sample time (min.) | Hydrolysis rates (mΔA/min) | | |
|---|---|---|---|
| | Not treated | Sonicated | A23187 |
| 0.5 | 3.58 | 30.50 | 20.05 |
| 1 | 11.76 | 109.98 | 90.13 |
| 1.5 | 31.17 | 216.81 | 203.39 |
| 2 | 59.28 | 329.58 | 342.61 |
| 2.5 | 101.42 | 469.00 | 506.75 |
| 3 | 155.66 | 591.66 | 656.18 |
| 3.5 | 229.36 | 742.88 | 881.96 |
| 4 | 317.90 | 843.14 | 1050.04 |

The procoagulant activity of control platelets, sonicated platelets and platelets treated with the calcium ionophore A23187 (1 μM). The samples with sonicated platelets or platelets treated with A23187 were diluted 50 times, before they were measured.

From the above, it is apparent that platelets possess a low procoagulant activity that can be increased somewhat by treatment with thrombin. Treatment with thrombin plus collagen increases this activity more. By incubation platelets with the calcium ionophore A23187 an enormous procoagulant activity is exposed, which is comparable with the activity exposed by sonication of the platelets.

As discussed in more detail below, this provides the basis for developing assays for determining the resting activity and/or excitability of platelets, and also allows for screening drugs which for example interfere with or inhibit the procoagulant activity of platelets by inhibiting the flip-flop mechanism in the platelet membrane.

Method for Determining the Resting Activity of Platelets

The resting activity of platelets is believed to be an indicator of thrombosis tendency. The higher the procoagulant activity of resting platelets is, the lower the threshold is at which an activated clotting factor will cause blood coagulation.

In general the assay may be carried out by collecting blood carefully to avoid platelet activation on citrate, or citrate plus additional compounds to keep the platelets in an unactivated state. The blood is diluted in saline sufficiently to prevent disturbance of the assay by the presence of erythrocytes. The diluted blood is mixed with a compound (substrate), which can be converted by a procoagulant phospholipid dependent enzyme(-complex). Examples of the substrate are prothrombin and factor X, which may be used in concentrations of 0.1–6 $\mu$M and 0.05–3 $\mu$M, respectively. Examples of phospholipid dependent enzyme-complexes are the factor X activating complex and prothrombinase. The components of the factor X activating complex are factor $IX_a$ (1–200 nM) and factor $VIII_a$ (0.1.–10 nM), and the components of the prothrombinase are factor $X_a$ (0.1–5 nM) and factor $V_a$ (0.1–10 nM). Then the enzyme-complex is added and after 0.5–4 minutes reaction time further activation of the substrate is stopped by addition of an inhibitor of the enzyme, for example EDTA, citrate or other compound that complexes the divalent cation on which the enzyme is dependent. To avoid disturbance of the measurement the erythrocytes should be removed. This can be achieved by centrifugation, or lysis of the cells by mixing the reaction mixture with ammonium bicarbonate.

The formed activated substrate is a measure for the procoagulant activity of the blood (platelets). The activated substrate can be measured by its ability to hydrolyse a chromogenic substrate. For example activated prothrombin (thrombin) can be measured by its ability to hydrolyse S2238 and activated factor X (factor $X_a$) by its ability to hydrolyse S2337, S2222, or $CH_3OCO$-D-CHG-Gly-Arg-pNA.acetate.

One preferred scheme for measuring procoagulant activity of resting platelets is as follows: Three reagents are required. Reagent 1 contains 6 $\mu$M prothrombin; reagent 2 contains 1.2 nM factor $X_a$, 1.2 nM factor $V_a$, 15 mM $CaCl_2$; and reagent 3 contains 10 mM EDTA (pH 8.0).

Blood is collected carefully to avoid platelet activation
  on ACD (183 mM glucose, 80 mM trisodium citrate, 52 mM citric acid); i.e. five parts blood are mixed with one part ACD. Glucose is present to keep the platelets in native unactivated form.

Platelets are isolated by gel filtration (see Lages et al., J. Lab. Clin. Med. 85:811–825 (1975)), or centrifugation (see Bevers et al., Biochim. Biophys. Acta 736:57–66 (1983)).

The further procedure is done at constant temperature, for example at 37° C. To 150 gl platelets is added 150 $\mu$l reagent 1 and the mixture is incubated during 5 minutes.

Then 150 $\mu$l reagent 2 is added to start the prothrombinase.

After 1, 2, 3 and 4 min. samples of 100 $\mu$l are taken and mixed with 500 $\mu$l reagent 3 in a cuvette to immediately terminate prothrombin activation.

The cuvette is placed in a thermostable spectrophotometer (for example at 37° C.) and thrombin is measured by addition of 20 $\mu$l S2238 and following the absorption increase at 405 nm.

By measuring platelets isolated from blood of a group of healthy individuals a set of values is obtained. By calculation of the mean and the standard deviation of these values, the borders can be determined, in which the normal resting platelet activity falls.

Method for Determining the Excitability of Platelets

The excitability of platelets is also believed to be an indicator for tendency of thrombosis. When for one reason or another the thrombin concentration in the blood rises, a dangerous situation may exist, especially when platelets have an increased excitability. In that case, a low concentration of thrombin will activate the platelets, whereas normal platelets would not generally have been activated.

In general the assay is similar as described above for the method for determining the resting activity of platelets. However, an additional step is required. Platelets are incubated with thrombin, or thrombin plus collagen, which are natural activators of platelets. By addition of thrombin, or thrombin plus collagen to the substrate and incubation of the platelets with this solution the same can be achieved, however, a reduction of the pipetting step is realized.

One preferred procedure to determine the excitability of platelets is as follows.

Platelets are isolated as described above.
Platelets are incubated with 4 nM thrombin, or 4 nM thrombin plus collagen (1 $\mu$g/ml) during 10 minutes at room temperature.

Then the procedure described above is continued.

To determine the normal excitability of platelets, blood from a group of healthy individuals is collected, platelets are isolated and the excitability of the platelets is determined. Then a set of values is obtained, which can be considered as normal values. From the values the statistics of normals can be calculated, which can be used to decide whether platelets of a single person have a higher excitablity then normal platelets.

Method for Screening Drugs which Inhibit the Flip-Flop Mechanism

To screen for drugs for their ability to inhibit platelet activation (flip-flop), this test can be used. Such a drug might be a useful medicine to treat patients with thrombosis, or a good prophylaxis for persons with thrombosis tendency.

The general procedure to assay for drugs, is as follows. Platelets are isolated as before. A mixture of the drug and thrombin, or thrombin plus collagen is prepared. Platelets are incubated with this mixture under standardized conditions and then the excitability of the platelets is measured as earlier is described. The necessary controls are incubation of platelets in the absence of the drug and an experiment with phospholipid vesicles of known composition in the presence and absence of the drug. The latter control is necessary to account for the effect of the drug on the assay itself.

A preferred scheme to screen for drugs which inhibit the flip-flop is based on the method to determine the excitability of platelets.

The preferred procedure described at method for determining the excitability of platelets is followed.

An additional step is included. The drug is mixed with the thrombin, or thrombin plus collagen. Then the procedure is continued as is described.

Necessary controls are:
  i) An experiment in the absence of the drug.
  ii) Test of the drug on the assay itself. Vesicles with high procoagulant activity are prepared and prothrombin activation is measured at a few phospholipid concentrations (0–0.4 µM) in the absence and presence of the drug. If the drug has effect on the assay a correction can be done to account for this effect.

Method for Determining the Procoagulant Activity of Platelets in Whole Blood In accordance with another aspect of the present invention there is provided a method for determining the procoagulant activity of platelets in whole blood. As discussed above, although the procoagulant activity of platelets can be measured in a simple assay, isolation of platelets require 1-2 hours, and thus is not ideal for clinical use. Determining the procoagulant activity of whole blood is preferred for that purpose. By having available a simple assay to measure platelet activity directly in whole blood a routine procedure can be used in the clinic to quickly test a large number of samples.

In general, blood is taken from a volunteer/subject and mixed with prothrombin. After incubation at a suitable temperature (e.g. 37° C.), the reaction is started by mixing whole blood and prothrombin with, for example, factor $V_a$, factor $X_a$ and $CaCl_2$. Samples are taken at predetermined increments and added to a tube with stop buffer. The red cells are thereafter spun down and removed because while red blood cells do not contribute to the measured activity, they do disturb the thrombin determination. The supernatant is then removed and added to cuvettes. Formed thrombin is measured after the addition of a chromogenic substrate.

In another embodiment, rather than removing red blood cells prior to the thrombin determination, they can be lysed as described in more detail in the examples below. However, when the cell-lysis approach is used it is necessary to dilute the whole blood in order to ensure that lysis is complete. The amount of the dilution depends on the size of the sample that is added to the stop buffer. In general, whole blood should be diluted at least about 16 times, and most preferably at least 20 times. In cases when the flip-flop reaction is complete (for example treatment with the calcium ionophore A23187), higher dilution (up to 200 times) may be necessary.

The following is one preferred scheme which may be used to measure procoagulant activity of whole blood. Three reagents are required. Reagent 1 contains 6 µM prothrombin; reagent 2 contains 1.2 nM factor $X_a$, 1.2 nM factor $V_a$, 15 niM CaCl2; and reagent 3, which either contains 10 mM EDTA (pH 8.0) (3A), or 10 mM EDTA (pH 8.0) plus 100 mM ammonium bicarbonate (3B).

Blood is collected on ACD (183 mM glucose, 80 mM trisodium citrate, 52 mM citric acid); i.e. five parts blood are mixed with one part ACD. Glucose is present to prevent platelet activation.

Blood is diluted 20 times in isotonic salt.

The diluted blood is incubated with for example thrombin plus collagen, or a drug and incubated 10 minutes at room temperature.

The further procedure is done at constant temperature, for instance at 37° C. To 150 µl diluted with blood is added 150 µl reagent 1 and the mixture is incubated during 5 minutes.

Then 150 µl reagent 2 is added to start the prothrombinase.

After 1, 2, 3 and 4 min. samples of 100 µl are taken and mixed 500 µl reagent 3 to immediately terminate prothrombin activation.

When reagent 3A is used the erythrocytes are removed by centrifugation; but using reagent 3B only a 2 min. incubation time is necessary to obtain complete lysis of the erythrocytes.

The mixture is transferred to a cuvette placed in a thermostable spectrophotometer (for example at 37° C.) and thrombin is measured by addition of 20 µl S2238 and following the absorption increase at 405 nm.

As described above the procoagulant activity of resting platelets and the excitability of platelets can be determined in blood samples obtained from a group of healthy subjects. The set of values obtained with these tests can be used to determine whether a single subject has a procoagulant activity of resting platelets, or excitability of platelets which deviates from normal values. Corrections for the platelet count can be done, either by counting the platelet in a counter, or by measuring the procoagulant activity after treatment with calcium-ionophore A23187, which is a measure for the platelet count.

It is also possible to screen drugs for their inhibiting effect on the flip-flop mechanism. In that case blood samples should be obtained from a group of healthy volunteers and the effect of the drug on the excitability of the platelets is determined.

The invention will be described in greater detail in the following examples.

EXAMPLE I

Determination of the Resting Activity of Platelets

Five parts blood are mixed with I part 183 mM glucose, 80 mM trisodium citrate, 52 mM citric acid. Three reagents are prepared: Reagent B contains 6 µM prothrombin; reagent A contains 1.2 nM factor $X_a$, 1.2 nM factor $V_a$, 15 mM CaCl2; and reagent 3 contains 10 mM EDTA (pH 8.0) plus 100 mM ammonium bicarbonate. The blood is diluted 20 times in isotonic salt. Then 100 µl diluted blood is mixed with 100 µl reagent B and incubated at 37° C. during 5 minutes. To this mixture is added 100 µl reagent A, the solution is well mixed and after 0.75 or 1.5 min. a sample of 250 µl is added to a cuvette with 500 µl reagent 3. Finally after 2 minutes time to allow complete lysis of the erythrocytes 50 µl S2238 is added to measure formed thrombin, which reflects the procoagulant activity of the platelets.

For clinical applications it is important that only a few pipetting step are necessary and thus large groups of individuals can be screened in a simple test.

By determining the procoagulant activity of a group of control individuals and a group of patients with proven thrombosis tendency, one can determine a threshold of the procoagulant activity of platelets, which indicates an increased tendency of thrombosis. For example, where a group of control subjects had an average procoagulant platelet activity of 5.52 m∆A/min, a group of patients, who underwent a bypass operation, had an average procoagulant platelet activity of 9.38 m∆A/min.

EXAMPLE II

Determination of the Excitability of Platelets

The same procedure as described in Example I is followed. However, to reagent B are added, for example, 4 nM thrombin and 1 µg/ml collagen.

By the presence of these natural activators of platelets, thrombin plus collagen, a litflited increase of procoagulant activity (excitability) will occur. This partial activation of platelets might vary from one group of individuals to another group. It is believed that with respect to a control group, a high excitability of platelets increases the risk of thrombosis.

EXAMPLE III

Method for Screening Drugs which Inhibit the Flip-Flop Reaction

Again the same procedure as described in Example I can be followed to measure the procoagulant activity of the platelets. The effect of drugs on platelet procoagulant activity can be studied by addition of the drug to the whole blood, to the diluted blood, or to reagent 1 and then following the same incubation scheme for each drug.

For example, blood is 20×diluted in isotonic salt to which is added 1 μg/ml aspirin. The mixture is incubated at 37° C. during 15 minutes. Then the procedure of Example 11 is followed. In that way it is possible to study the effect of aspirin on the excitability of platelets by thrombin plus collagen. If, for example, the excitability of the platelets is decreased by more than about 50%, then one can conclude that the candidate drug inhibits or otherwise interferes with the flip-flop reaction.

EXAMPLE IV

Measurement of Platelets Activity in Whole Blood

In a first trial, reagents A and B were prepared as follows: reagent A contained 240 pM factor $V_a$, 240 pM factor $X_a$ and 15 mM $CaCl_2$. Reagent B contained 6 μM prothrombin. The experimental approach was, the whole blood was mixed with reagent B and the reaction was started with reagent A and then the prothrombinase activity was measured. The blood was diluted as indicated in Table VIII. The pipetting scheme was: 300 μl reagent B was mixed with 300 μl diluted whole blood. After 5 minutes preincubation at 37° C. 300 μl reagent A was added. Samples of 100 μl were taken after 0.5, 1, 1.5, 2, 2.5, 3, 3.5 and 4 min. reaction time and added to tubes with 900 μl stopbuffer (10 mM EDTA). The red cells were spun down (Eppendorf) and 900 μl of the supernatants were added to the cuvettes. Formed thrombin was measured by addition of 18 μl S2238. In Table VIII the results are shown.

Because in the cases with the least dilution a clot was formed, 0.5 mM gly-pro-arg-pro was added to the reaction mixture and the blood tested as before.

TABLE VIII

Procoagulant activity of platelets measured in whole blood.

| Reaction time (min) | Hydrolysis rates (mΔA/DT); The blood dilution was: | | | |
|---|---|---|---|---|
| | 20 × | 5 × | 2 × | 2 × plus GPAP |
| 0.5 | 1.26 | 2.35 | 3.63 | 5.28 |
| 1 | 2.76 | 6.74 | 12.86 | 14.45 |
| 1.5 | 5.34 | 14.63 | 25.42 | 29.26 |
| 2 | 8.63 | 23.66 | 38.53 | 45.15 |
| 2.5 | 12.94 | 35.93 | 55.22 | 64.96 |
| 3 | 16.60 | 51.14 | clot | 85.27 |
| 3.5 | 22.95 | 65.73 | | 106.36 |
| 4 | 29.59 | clot | | 118.00 |

Table VIII shows that the signal is not linear with the amount of added blood. It was not possible to avoid the centrifugation step to remove the red cells, because these cells disturbed the measurement.

Further tests were done in the following way. To 270 μl whole blood was added 30 μl gly-pro-arg-pro (10 mill) and the procoagulant activity was measured as before (control). The effect of addition the calcium ionophore A23187 to the blood was also studied. The following mixture was prepared: 30 μl whole blood, 267 μl standard buffer, 3 μl A23187 (100 μM) and this solution was tested after 5 minutes at room temperature as described above (see Table IX).

TABLE IX

Procoagulant activity of platelets. Measurement in whole blood.

| Reaction time (min.) | Hydrolysis rates (mΔA/min) | |
|---|---|---|
| | Control | Plus A23187 |
| 0.5 | 1.26 | 5.43 |
| 1 | 4.28 | 22.98 |
| 1.5 | 8.20 | 56.16 |
| 2 | 11.41 | 104.53 |
| 2.5 | 13.47 | 165.50 |
| 3 | 16.10 | 235.75 |
| 3.5 | 17.76 | 320.44 |
| 4 | 21.10 | 416.78 |

As can be seen from the above, calcium-ionophore A23187 increases the activity enormously. This activity is determined by the total amount of platelets, because complete flip-flop of all available phospholipids is induced by the ionophore and the activity is determined by the total amount of phospholipids and the percentage phosphatidyl serine in the phospholipid membrane. Phosphatidyl serine is present in constant amounts in the cells so the maximal procoagulant activity is only dependent on the total amount of phospholipids. Thus the activity induced by A23187 can be used as platelet count and corrections can be made to account for variations in platelet concentration.

EXAMPLE V

To develop a simpler approach to determine the procoagulant activity of whole blood, a stopbuffer of ammonium bicarbonate plus EDTA was used. Red blood cells lyse in ammonium bicarbonate because this salt is not fully ionized in water. In the aqueous solution are present the uncharged small molecules $NH_3$ and $CO_2$, which pass the erythrocytes membrane. In the cell these molecules react with water and ions are formed again and so the ionic strength in the cell increases. To compensate for the increased ionic strength water diffuses into the cell and finally the cell lyses. By sub-sampling in ammonium bicarbonate the erythrocytes lyse and do not disturb the chromogenic measurements.

First, how changing the buffer affects the hydrolysis rate of S2238 by thrombin was determined. Table X shows that this is the case.

TABLE X

| S2238 (μl) | Buffer | Hydrolysis rate (mΔA/min) | |
|---|---|---|---|
| 20 | Standard | 73.42 | 74.12 |
| 50 | | 75.42 | 75.73 |
| 20 | Lyse | 51.44 | 51.46 |
| 50 | | 57.10 | 56.60 |

The hydrolysis rate of S2238 by thrombin in either 175 mM NaCl, 50 mM Tris-HCl, 10 mM EDTA (pH 7.9) (=standard stopbuffer), or 100 mM ammonium bicarbonate, 10 mM EDTA (pH 8.0) (=lyse stopbuffer). In the cuvette were pipetted 100 μl thrombin (ι8 nM), S2238 as indicated and buffer to a final volume of 1 ml.

The experiments shown in Table XI are done in two ways, i.e. termination of the reaction either by sub-sampling in standard stopbuffer, or by sub-sampling in ammonium bicarbonate plus EDTA. In case of sub-sampling in standard stopbuffer the erythrocytes were spun down and thrombin formation was measured in the supernatant. In the case with ammonium bicarbonate buffer the centrifuge step was omitted.

TABLE XI

Measuring of procoagulant phospholipids in whole blood. The blood was collected in 3.8% sodium citrate (1 part citrate, nine parts blood). The blood was sub-sampled in either 175 mM NaCl, 50 mM Tris-HCl, 10 mM EDTA (pH 7.9), or 100 mM ammonium bicarbonate, 10 mM EDTA (pH 8.0). In case of sub-sampling in standard stopbuffer the red cells were spun down and thrombin was measured in the supernatant. In the second case the centrifuge-step was omitted.

| | Reaction time (min) | Hydrolysis rates (m$\Delta$A/min) | |
|---|---|---|---|
| | | Standard stopbuffer | Ammonium bicarbonate |
| (200 µl) | 1 | 50.62 | 45.00 |
| | 2 | 159.42 | 135.02 |
| | 3 | 277.40 | 214.41 |
| | 4 | 416.44 | 312.65 |
| (200 µl) "aged blood" | 1 | 233.90 | 208.88 |
| | 2 | 708.74 | 600.81 |
| | 3 | 1235.58 | 1011.16 |
| | 4 | 1823.44 | 1236.48 |
| (100 µl) "aged blood" | 1 | 359.93 | 373.15 |
| | 2 | 1189.99 | 949.34 |
| | 3 | 1628.35 | 1424.79 |
| | 4 | 1990.68 | 1796.25 |
| (100 µl) "aged blood" | 1 | 153.07 | 127.14 |
| | 2 | 440.32 | 351.85 |
| | 3 | 727.71 | 565.30 |
| | 4 | 1025.02 | 799.64 |

To increase the sensitivity of the assay, reagents with higher amounts of factor $X_a$ and factor $V_a$ were prepared (see section on "Measurement of Small Concentrations of Phospholipids"). For that reason reagents A with 1.2 nM factor $X_a$, 1.2 nM factor $V_a$ and 15 mM CaCl$_2$ were prepared. Reagent B with 6 µM prothrombin was used. These reagents were used in the next experiments examples VI-IX.

EXAMPLE VI

Testing Platelets in Whole Blood with the Simplified Procedure

The experiment described below shows that procoagulant activity of platelets in whole blood can be measured in a simple way, which is better suited for clinical use, because only two time-dependent pipetting steps are required. By using whole blood, one avoids the isolation procedure of platelets, which is time consuming and moreover increases the risk of platelet activation. Care should be taken to avoid activation of the blood. Then one part of in saline diluted blood is mixed with one part prothrombin (reagent B). After a few minutes incubation at, for example, 37° C. one part reagent A is added, and after predetermined reaction times, samples are mixed with lyse stop buffer. Formed thrombin is measured by addition of a chromogenic thrombin substrate after sufficient time to permit complete lysis of erythrocytes.

One preferred scheme for determination of procoagulant activity of whole blood is the following example. Blood is diluted 20 times in saline. All reagents are preincubated at 37° C. during 5 minutes to be sure that the reaction temperature is precisely 37° C. To 150 il diluted blood is added to 150 µl reagent B, then to start the reaction 150 µl reagent A is added. Samples of 100 µl are taken at 1, 2, 3 and 4 min reaction time and mixed with 500 µl 100 mM ammonium bicarbonate, 10 mM EDTA (pH 8.0). Formed thrombin is measured after 2 minutes by addition of 20 µl S2238.

In one experiment, blood was taken from healthy persons before and after physical exertion. In Persons 1-5 the blood was collected on citrate, whereas in cases 6-8 the blood was collected on ACD (citrate, citric acid, glucose). In Table XII the results are shown.

In FIG. 1-8 the results are plotted of the blood sample (persons 1-8 respectively) taken before and after the physical exertion.

One can notice that the effect of physical exertion is almost the same in all cases. In all cases but one (person 4) the procoagulant activity of the platelets was higher after the exertion. The reason why the procoagulant activity of the platelets is higher after the exertion is not clear.

We also notice that the procoagulant activity of the platelets in blood collected on ACD is somewhat lower than in the other cases, however, this effect is not very pronounced. The effect of ACD can be noticed very well after a few hours (not shown). Having present no glucose in the blood sample, the platelets will activate within a few hours (see Table XI), whereas in the presence of glucose the platelets keep their low procoagulant activity during this time. For that reason it is necessary to measure blood that contains no added glucose within about an hour, because after a longer incubation time the platelets will be more or less activated and thus activities will be measured, which are above the "real" values of the patient/subject. A false positive indication for risk of thrombosis would be the result.

TABLE XII

| Reaction time (min) | | Hydrolysis rates (m$\Delta$A/min) | | | Blanc = no phospholipids |
|---|---|---|---|---|---|
| | | Before | | After | |
| Person 1 | 1 | 9.71 | 11.08 | 48.74 | 41.52 | 2.74 |
| | 2 | 34.53 | 35.24 | 118.09 | 112.00 | 5.12 |
| | 3 | 81.02 | 85.72 | 205.29 | 186.83 | 10.94 |
| | 4 | 141.43 | 151.37 | 316.40 | 288.72 | 17.23 |
| Person 2 | 1 | 39.04 | 41.82 | 47.01 | 51.05 | |
| | 2 | 100.92 | 108.80 | 132.48 | 139.36 | |
| | 3 | 185.22 | 188.79 | 237.34 | 246.18 | |
| | 4 | 261.89 | 274.28 | 362.37 | 369.94 | |
| Person 3 | 1 | 34.56 | 35.19 | 72.55 | 74.76 | |
| | 2 | 91.55 | 94.93 | 208.82 | 212.38 | |
| | 3 | 163.02 | 167.22 | 359.63 | 362.79 | |
| | 4 | 245.49 | 241.66 | 548.19 | 542.21 | |
| Person 4 | 1 | 73.51 | 69.98 | 78.05 | 70.18 | |
| | 2 | 191.03 | 184.30 | 189.65 | 185.97 | |
| | 3 | 314.95 | 309.85 | 310.60 | 313.67 | |
| | 4 | 443.35 | 423.10 | 420.40 | 442.33 | |
| Person 5 | 1 | 43.32 | 38.55 | 57.02 | 61.53 | |
| | 2 | 111.01 | 109.65 | 159.98 | 172.05 | |
| | 3 | 186.24 | 196.02 | 285.68 | 317.79 | |
| | 4 | 267.61 | 265.60 | 410.51 | 443.69 | |
| Person 6 | 1 | 13.24 | 14.08 | 38.80 | 41.47 | |
| | 2 | 39.82 | 40.70 | 108.43 | 108.34 | |
| | 3 | 68.68 | 67.77 | 165.53 | 166.01 | |
| | 4 | 105.44 | 109.99 | 263.61 | 286.09 | |
| Person 7 | 1 | 18.12 | 18.38 | 42.59 | 39.35 | |
| | 2 | 44.36 | 45.03 | 100.55 | 94.77 | |
| | 3 | 74.71 | 75.30 | 162.60 | 155.76 | |
| | 4 | 129.25 | 118.54 | 250.39 | 255.83 | |
| Person 8 | 1 | 24.98 | 25.78 | 66.47 | 66.80 | |
| | 2 | 71.48 | 70.51 | 175.01 | 168.64 | |
| | 3 | 128.47 | 128.30 | 285.20 | 286.34 | |
| | 4 | 173.01 | 184.79 | 400.85 | 388.61 | |

Measuring of procoagulant phospholipids in whole blood. A simplified procedure was used (see text).

EXAMPLE VII

Testing Platelets of "Thrombosis" Patients

The simplified platelet test using the ammonium bicarbonate stop buffer was used to measure procoagulant activity of platelets in whole blood from patients who were treated with Sintromitis to inhibit partly the synthesis of vitamin K dependent clotting factors. By reducing the concentration of vitamin K dependent clotting factors in blood, blood coagulation is partly inhibited and thus, for example, the risk of thrombosis is reduced. The level of the vitamin K dependent clotting factors was measured regularly at the Thrombosis Service of the Academic Hospital of Maastricht. The blood was collected on ACD to keep the platelets as native as possible. In Table XIII the results are shown.

Figure 17:
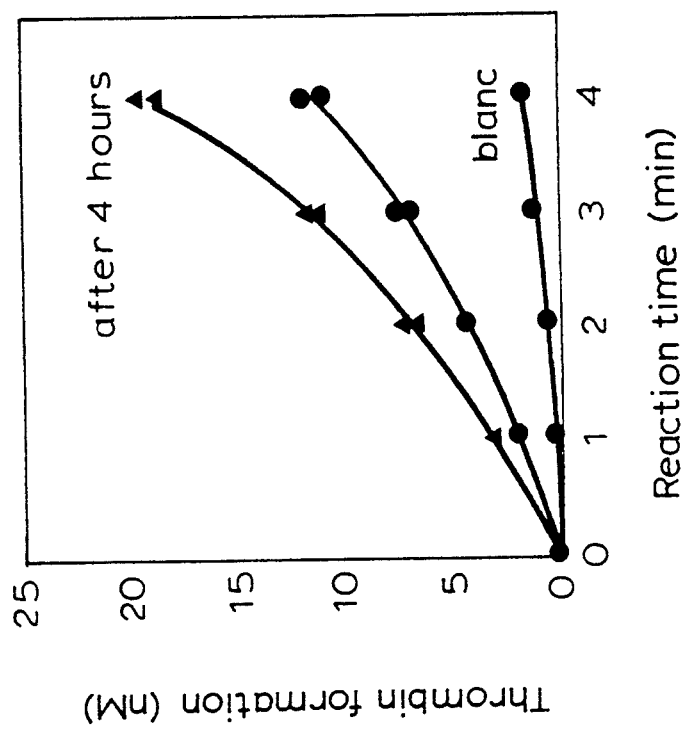
FIGS. 17 and 18A-H show measurement of procoagulant activity of whole blood of thrombosis patients.
Figure 18A:
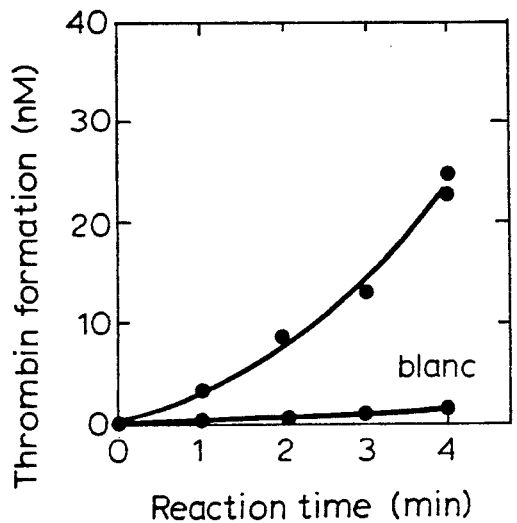
Figure 18B:
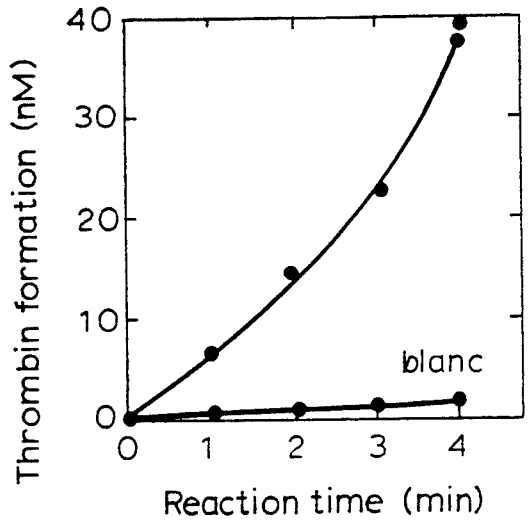
Figure 18C:
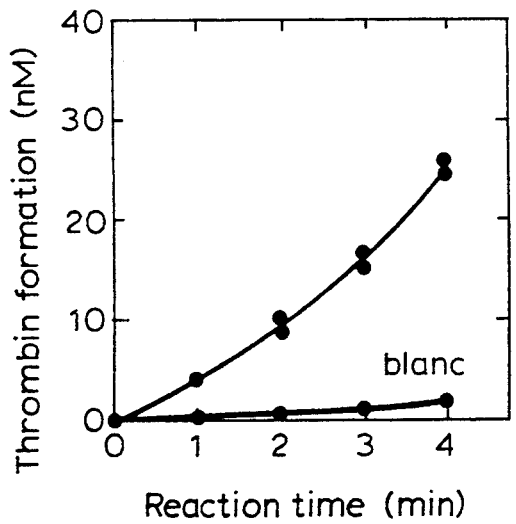
Figure 18D:
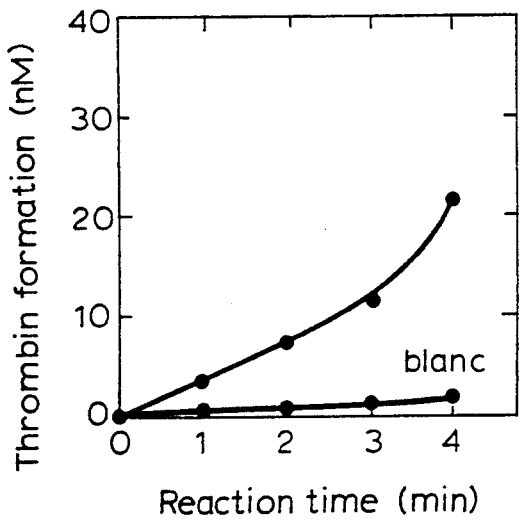
Figure 18E:
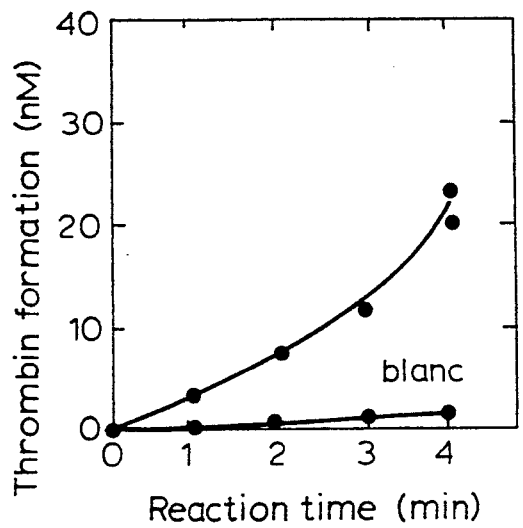
Figure 18F:
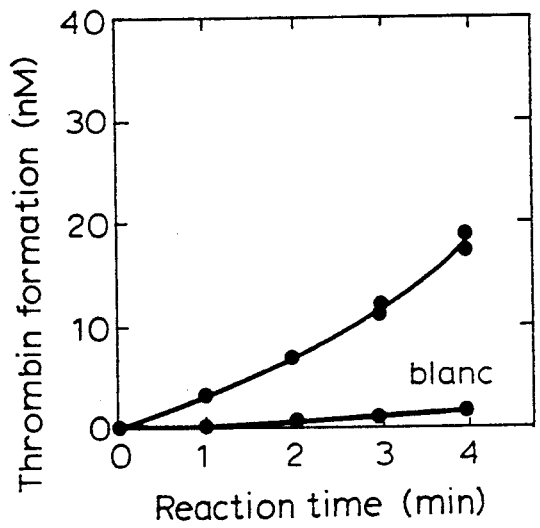
Figure 18G:
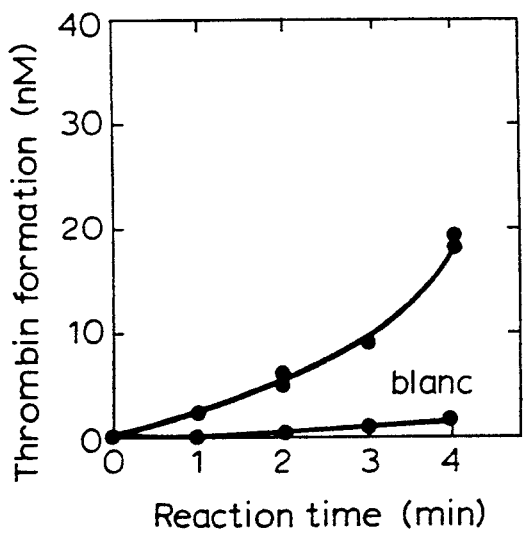
Figure 18H:
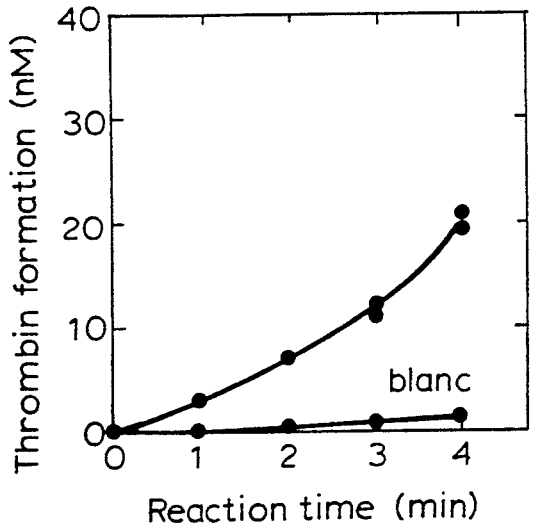

In FIGS. 17-18 the results are plotted (patients 1 and 2-9 respectively). In one case (FIG. 17) the measurement was repeated after 4 hours to test the stability of the platelets. One can notice that after 4 hours the procoagulant activity was increased somewhat, in spite of the presence of glucose in the sample. In FIG. 17 this is illustrated.

In FIG. 18 we have plotted the results of the patients 2-8. One can notice that the shape of the curve is somewhat different than in the cases of earlier results. The rate of thrombin formation is linear up to 2 min. and then strongly increases. Whether this is due to the treatment, to the age, or the sickness of the patients is not clear. We also notice that the procoagulant activity of the platelets in almost all cases was higher than platelets of healthy volunteers (control).

Table XIII shows that in all cases the platelets of the "patients" had a higher procoagulant activity then control platelets. It is believed that these results are a strong indication that the resting procoagulant activity of patient platelets is higher than the resting procoagulant activity of control platelets. To prove that an increased procoagulant activity of platelets is an indication for risk of thrombosis, it is preferable to determine this activity in a well defined large group.

To have statistically significant differences between groups of patients it is also preferred that the confidence intervals do not overlap. This will be the case sooner when the differences are larger. So the smaller the difference, the larger the groups should be to prove statistical significant differences.

Table XIII indicates that, as far as conclusions can be drawn from such a small group of subjects, patients with a proven risk of thrombosis have a higher procoagulant activity of resting platelets than control subjects.

TABLE XIII

| | Time (min.) | Hydrolysis rates (mΔA/min) | | | | |
|---|---|---|---|---|---|---|
| Control | 1 | 7.72 | 7.17 | | | |
| | 2 | 25.91 | 27.71 | | | |
| | 3 | 55.62 | 52.09 | | | |
| | 4 | 121.60 | 115.73 | | | |
| Control | 1 | 9.00 | 11.86 | 12.52 | | |
| | 2 | 39.70 | 37.05 | 40.14 | | |
| | 3 | 68.47 | 64.60 | 69.50 | | |
| | 4 | 109.43 | 108.06 | 113.53 | | |
| Patient 1 | 1 | 19.28 | 19.64 | 29.05 | 31.80 | |
| | 2 | 43.39 | 44.17 | 66.65 | 73.32 | Measured after 4 |
| | 3 | 72.05 | 68.50 | 110.62 | 115.33 | hours storage at |
| | 4 | 110.29 | 116.66 | 185.23 | 194.06 | room temperature. |
| Patient 2 | 1 | 35.72 | 35.67 | | | |
| | 2 | 86.08 | 84.50 | | | |
| | 3 | 128.37 | 129.03 | | | |
| | 4 | 245.48 | 227.65 | | | |
| Patient 3 | 1 | 61.12 | 63.96 | | | |
| | 2 | 137.84 | 139.96 | | | |
| | 3 | 221.89 | 221.16 | | | |
| | 4 | 371.26 | 386.82 | | | |
| Patient 4 | 1 | 39.42 | 41.14 | | | |
| | 2 | 91.73 | 98.75 | | | |
| | 3 | 150.94 | 160.34 | | | |
| | 4 | 241.42 | 254.03 | | | |
| Patient 5 | 1 | 34.27 | 36.01 | | | |
| | 2 | 70.86 | 73.14 | | | |
| | 3 | 110.89 | 113.65 | | | |
| | 4 | 211.53 | 210.09 | | | |
| Patient 6 | 1 | 32.27 | 33.60 | | | |
| | 2 | 75.82 | 72.68 | | | |
| | 3 | 116.35 | 119.17 | | | |
| | 4 | 199.11 | 230.86 | | | |
| Patient 7 | 1 | 31.09 | 31.95 | | | |
| | 2 | 71.64 | 70.99 | | | |
| | 3 | 119.51 | 111.95 | | | |
| | 4 | 188.82 | 177.31 | | | |
| Patient 8 | 1 | 25.23 | 23.96 | | | |
| | 2 | 60.17 | 51.26 | | | |
| | 3 | 93.26 | 88.32 | | | |
| | 4 | 187.83 | 180.51 | | | |
| Patient 9 | 1 | 29.97 | 33.45 | | | |
| | 2 | 69.48 | 74.14 | | | |
| | 3 | 110.59 | 118.09 | | | |
| | 4 | 193.95 | 210.62 | | | |

Measuring of procoagulant phospholipids in whole blood of patients of Thrombosis Service.

EXAMPLE VIII

Blood is diluted 20 times in saline. Then, 50 μl diluted blood is mixed with 50 μl prothrombin (6 μM). After a short preincubation time to prewarm the mixture 50 μl activation mixture is added lit (t=0). The activation mixture contains 1.2 nM factor $V_a$, 1.2 nM factor $X_a$ and 15-30 mM $CaCl_2$. After 1-4 minutes 500 μl stopbuffer is added (100 mM ammonium bicarbonate, 10 mM EDTA). Then after about I to 2 minutes a chromogenic substrate is added to measure formed thrombin.

Possible adaptations are:

Addition of protamine, which makes the assay insensitive for heparin.

The stopbuffer contains ammonium bicarbonate, which is necessary to lyse the erythrocytes. It is possible to add the chromogenic substrate to the stopbuffer and to avoid a sub-sampling step. However, it takes a short time to lyse the erythrocytes and because these cells disturb the measurement, thrombin formation cannot be measured before I to 2 minutes after stopping the reaction. So a large excess of chromogenic substrate should be present, otherwise the substrate is exhausted before one can measure the formed thrombin. One can avoid this problem by using platelet rich plasma.

A possible way to standardize the amount of platelets is preincubation with the calcium ionophore A23187, which causes complete randomization of the phosphatidyl serine over both membrane leaflets and the maximal amount of procoagulant phospholipids are exposed. To measure the activity in this case the sample should preferably be diluted at least about 100 times.

Procoagulant activities of whole blood from healthy subjects, from persons who underwent physical exertion and from patients who were treated with sintromitis are shown. In Table XIV the results are summarized. It is important that the blood is collected carefully to avoid activation of the platelets. Also it is necessary to measure the activity within an hour otherwise the platelets will become activated. Only if one collects the blood in ACD (sodium citrate, citric acid, glucose) the platelets are more stable and can be kept unactivated a few hours. In Table XIV also some statistics are shown. The most important results are: physical exertion causes an 2 to 4-fold increase of the procoagulant activity and the procoagulant activity of the "sintromitis"patients are 2-1.5 times higher than the control group.

Besides the conclusions already drawn in examples VI-VIII another important point is, the differences between the groups is most pronounced when the reaction time is short. This is believed to be due to the activation of the platelets in the reaction mixture by formed thrombin. For this reason it is better to use short reaction times in order to measure the initial procoagulant activity of the platelets and not the activity induced in the reaction vessel.

TABLE XIV

Procoagulant activity of whole blood. Blood was diluted 20 times in saline. Fifty μl diluted blood was mixed with 50 μl prothrombin. After a few minutes equilibration at 37° C. 50 μl activation mixture was added. The prothrombinase was terminated after 1, 2, 3 and 4 minutes reaction time by addition of 500 μl stop buffer. Formed thrombin was measured by addition of 20 μl S2238 after 1-2 minutes to lyse the erythrocytes

| | Hydrolysis rates (mΔA/min) after | | | |
|---|---|---|---|---|
| | 1 | 2 | 3 | 4 min. |
| Healthy subjects | | | | |
| 1 | 17.25 | 57.83 | 89.28 | 151.02 |
| 2 | 14.42 | 48.42 | 115.72 | 203.28 |
| 3 | 45.41 | 129.42 | 229.20 | 338.10 |
| 4 | 18.96 | 55.88 | 94.70 | 149.51 |
| 5 | 25.33 | 62.04 | 104.11 | 171.97 |
| 6 | 35.23 | 98.54 | 178.20 | 248.31 |
| 7 | 27.75 | 77.61 | 134.51 | 318.58 |
| 8 | 22.79 | 62.26 | 108.18 | 181.21 |
| Statistics | | | | |
| Mean | 25.89 | 74.00 | 131.74 | 220.25 |
| Std. deviation | 10.24 | 27.29 | 48.42 | 73.95 |
| Std. error | 3.63 | 9.65 | 17.12 | 26.15 |
| | Ratio hydrolysis rates before and after | | | |
| Physical exertion | | | | |
| 2 | 4.3415 | 3.2978 | 2.35-17 | 2.0667 |
| 3 | 2.1120 | 2.2587 | 2.18-76 | 2.2383 |
| 4 | 2.9381 | 2.6921 | 2.42-98 | 2.5516 |
| 5 | 2.2449 | 2.1850 | 2.12-23 | 2.0429 |
| 6 | 2.6255 | 2.4202 | 2.22-59 | 2.2064 |
| | Hydrolysis rates (mΔA/min) after | | | |
| | 1 | 2 | 3 | 4 min. |
| "Thrombosis patients" | | | | |
| 9 | 27.01 | 60.77 | 97.54 | 157.50 |
| 10 | 49.55 | 118.38 | 178.64 | 328.35 |
| 11 | 86.81 | 192.79 | 307.48 | 526.11 |
| 12 | 55.91 | 132.19 | 216.03 | 343.84 |
| 13 | 48.77 | 99.94 | 155.83 | 292.60 |
| 14 | 45.71 | 103.06 | 163.45 | 298.40 |
| 15 | 43.75 | 98.98 | 160.63 | 254.09 |
| 16 | 34.14 | 77.33 | 126.02 | 255.63 |
| 17 | 44.01 | 99.67 | 158.70 | 280.77 |
| Statistics | | | | |
| Mean | 48.41 | 109.24 | 173.81 | 304.14 |
| Std. deviation | 16.74 | 37.55 | 59.80 | 99.06 |
| Std. error | 5.58 | 12.52 | 19.90 | 33.02 |

EXAMPLE IX

Procoagulant Activity of Platelets from Different Patient Groups

Four different patient groups and a control group were tested. The patient groups were: those who underwent a bypass operation, those who had a coronary infarction, those with atrium fibrillation, and those with deep venous thrombosis. Lyophilized reagents were used with the composition described in Example VIII. The protocol was: at t=0' 100 μl prothrombin, or prothrombin+IIa (10 nM)+collagen (10 μg/ml), or prothrombin+calcium ionophore A23187 (5 μM) was mixed with 100 μl diluted blood (20 times in saline, but in case of ionophore 200 times); at t=5'100 μl FXa.F-Va.Ca was added; at t=5'45" and 6'30"100 μl was mixed with 500 μl EDTA-ammonium bicarbonate; and after 2' formed thrombin was measured by addition of 20 μl S2238.

In Table XV the average values are given of all groups and moreover some statistical values are given. Besides the hydrolysis rates, the ratios between the no addition rates and the ionophore rates, and between the IIa/collagen rates and the ionophore rates are given. These values are an indication of the percentage activation of the platelets.

The results in Table XV show that the procoagulant activity (no addition; 45 sec.) of all patients groups is higher than the activity of the control group. When one looks at the ratios we notice that the values in case of the patient groups are about three times higher than control group values. These noticed differences are less or almost absent when we look at the 90 sec. values. This indicates that the 45 sec. values are more discriminative than the 90 sec. values. The procoagulant activity induced by thrombin plus collagen is more or less the same in all groups, indicating that patient platelets are less excitable than control platelets, very likely because patient platelets already are activated to some extent.

Thus, it can be seen that a platelet assay is developed which requires only two time dependent pipetting steps, provided that platelet rich plasma is used. The preparation of platelet rich plasma can be standardized in a clinical laboratory by centrifugation for a fixed time and gravity (determined by revolutions per minute and radius). If one still prefers the use of whole blood it is necessary to use stop buffer with a large excess of chromogenic substrate, or an additional sub-sampling step is required.

It is also possible to change the volumes of the reagents in order to adapt the assay for an automate, by, for example, take 100 μl dilute blood and 100 μl prothrombin, mix and incubate 3 minutes, add 100 μl activation mixture and add 600 μl stopbuffer at 3.75 or 4.5 minutes. Finally add 50 μl chromogenic substrate 1.5 minutes after the addition of the stopbuffer. This last step is necessary to account for complete lysis of the erythrocytes.

For practical clinical use it is preferred that lyophilized reagents can be used.

TABLE XV

Average procoagulant activities of platelets from 4 patient groups and a control group. Besides the absolute hydrolysis rates, statistical values and ratios are given (see text for further explanation).

| Patients groups | | Reaction Time is 45 sec. | | | | | Reaction time is 90 sec. | | | | |
|---|---|---|---|---|---|---|---|---|---|---|---|
| | | Hydrol. rates (mΔA/min) | | | ratio | ratio | Hydrol. rates (mΔA/min) | | | ratio | ratio |
| | | no addi | II$_a$/col | A23187 | no addi | II$_a$/col | no addi | II$_a$/col | A23187 | no addi | II$_a$/col |
| Bypass operation; | average | 9.38 | 17.37 | 37.44 | 0.27 | 0.51 | 20.49 | 24.64 | 139.64 | 0.15 | 0.18 |
| 31 individuals. | std. deviation | 4.29 | 3.95 | 12.72 | 0.11 | 0.18 | 11.30 | 9.22 | 44.05 | 0.07 | 0.06 |
| | variance | 18.44 | 15.61 | 161.79 | 0.01 | 0.03 | 127.79 | 85.08 | 1940.34 | 0.00 | 0.00 |
| | std. error | 0.77 | 0.71 | 2.28 | 0.02 | 0.03 | 2.03 | 1.66 | 7.91 | 0.01 | 0.01 |
| coronary | average | 9.18 | 18.62 | 39.00 | 0.25 | 0.50 | 19.67 | 27.11 | 141.71 | 0.15 | 0.20 |
| infarction; | std. deviation | 5.68 | 4.09 | 10.42 | 0.17 | 0.15 | 15.93 | 9.72 | 31.23 | 0.13 | 0.09 |
| 31 individuals. | variance | 32.30 | 16.74 | 108.52 | 0.03 | 0.02 | 253.62 | 94.49 | 975.18 | 0.02 | 0.01 |
| | std. error | 1.02 | 0.73 | 1.87 | 0.03 | 0.03 | 2.86 | 1.75 | 5.61 | 0.02 | 0.02 |
| atrium | average | 8.50 | 16.52 | 34.32 | 0.26 | 0.51 | 17.34 | 22.87 | 129.08 | 0.14 | 0.19 |
| fibrillation; | std. deviation | 2.24 | 2.52 | 10.54 | 0.09 | 0.13 | 4.49 | 5.18 | 33.83 | 0.04 | 0.05 |
| 19 individuals. | variance | 5.01 | 6.33 | 111.10 | 0.01 | 0.02 | 20.19 | 26.79 | 1144.65 | 0.00 | 0.00 |
| | std. error | 0.51 | 0.58 | 2.42 | 0.02 | 0.03 | 1.03 | 1.91 | 7.76 | 0.01 | 0.01 |
| deep venous | average | 7.56 | 16.23 | 32.28 | 0.28 | 0.61 | 13.62 | 20.74 | 120.61 | 0.13 | 0.20 |
| thrombosis; | std. deviation | 1.13 | 1.67 | 14.99 | 0.13 | 0.30 | 3.04 | 3.22 | 49.17 | 0.04 | 0.10 |
| 5 individuals. | variance | 1.29 | 2.79 | 224.61 | 0.02 | 0.09 | 9.26 | 10.40 | 2417.95 | 0.00 | 0.01 |
| | std. error | 0.51 | 0.75 | 6.70 | 0.06 | 0.14 | 1.36 | 1.44 | 21.99 | 0.02 | 0.04 |
| control group; | average | 5.52 | 15.29 | 64.78 | 0.09 | 0.26 | 12.11 | 20.87 | 215.99 | 0.06 | 0.10 |
| 17 individuals. | std. deviation | 1.62 | 1.69 | 19.40 | 0.03 | 0.08 | 3.54 | 3.99 | 60.16 | 0.02 | 0.03 |
| | variance | 2.63 | 2.86 | 376.37 | 0.00 | 0.01 | 12.52 | 15.95 | 3619.26 | 0.00 | 0.00 |
| | std. error | 0.39 | 0.41 | 4.71 | 0.01 | 0.02 | 0.86 | 0.97 | 14.59 | 0.00 | 0.01 |

What is claimed is:

1. A method for determining the risk of thrombosis in a patient by determining the procoagulant activity of resting platelets comprising:
   (a) mixing a sample containing platelets from a patient with a substrate which can be converted by a procoagulant phospholipid dependent enzyme or enzyme complex;
   (b) contacting and reacting the mixture of step (a) with the enzyme or enzyme complex to form an activated substrate;
   (c) determining the amount of the formed activated substrate in the sample; and
   (d) comparing the amount of formed activated substrate from the patient with the amount of formed activated substrate from one or more control individuals.

2. The method of claim 1, wherein the platelets from the patient are isolated in a manner which keeps the platelets in an unactivated state.

3. The method claim 1, wherein the substrate is selected from the group consisting of prothrombin and factor X.

4. The method of claim 1, wherein the procoagulant phospholipid dependent enzyme or enzyme complex is selected from the group of consisting factor X activating complex and prothrombinase.

5. The method of claim 1, wherein the amount of formed activated substrate in the sample is determined by its ability to hydrolyse a chromogenic substrate.

6. The method of claim 1, wherein the sample containing platelets comprises whole blood taken from the patient.

7. The method of claim 6, further comprising the step of removing red blood cells from the whole blood prior to determining the amount of formed activated substrate in the sample.

8. The method of claim 6, wherein the whole blood is diluted and the red blood cells are lysed prior to determining the amount of formed activated substrate in the sample.

9. The method of claim 8, wherein the whole blood is diluted at least about 16 times.

10. The method of claim 8, wherein the whole blood is diluted at least about 20 times.

11. A method for determining the risk of thrombosis in a patient by determining the excitability of platelets comprising:
   (a) incubating a sample containing platelets from a patient with thrombin or thrombin plus collagen;
   (b) mixing the resulting product of step (a) with a substrate which can be converted by a procoagulant phospholipid dependent enzyme or enzyme complex;
   (c) contacting and reacting the mixture of step (a) with the enzyme or enzyme complex to form an activated substrate;
   (d) determining the amount of the formed activated substrate in the sample; and
   (e) comparing the excitability of platelets from the patient with the excitability of platelets from one or more control individuals.

12. The method of claim 11, wherein the platelets from the patient are isolated in a manner which keeps the platelets in an unactivated state.

13. The method of claim 11, wherein the substrate is selected from the group consisting of prothrombin and factor X.

14. The method of claim 11, wherein the procoagulant phospholipid dependent enzyme or enzyme complex is selected from the group consisting of factor X activating complex and prothrombinase.

15. The method of claim 11, wherein the amount of formed activated substrate in the sample is determined by its ability to hydrolyse a chromogenic substrate.

16. The method of claim 11, wherein the sample containing platelets comprises whole blood taken from the patient.

17. The method of claim 16, further comprising the step of removing red blood cells from the whole blood prior to determining the amount of formed activated substrate in the sample.

18. The method of claim 16, wherein the whole blood is diluted and the red blood cells are lysed prior to determining the amount of formed activated substrate in the sample.

19. The method of claim 18, wherein the whole blood is diluted at least about 16 times.

20. The method of claim 18, wherein the whole blood is diluted at least about 20 times.

21. A method for determining if an agent will effectively inhibit platelet activation comprising:
   (a) incubating a sample containing platelets with (i) thrombin or thrombin plus collagen; and (ii) a said agent;
   (b) mixing the resulting product of step (a) with a substrate which can be converted by a procoagulant phospholipid dependent enzyme or enzyme complex;
   (c) contacting and reacting the mixture of step (b) with the enzyme or enzyme complex to form an activated substrate;
   (d) determining the amount of the formed activated substrate in the sample; and
   (e) comparing the amount of formed activated substrate from the sample containing said agent with the amount of formed activated substrate from an agent-free sample.

22. The method of claim 21 further comprising the step of subtracting the amount of formed activated substrate due to said agent itself form the amount of formed activated substrate determined in step (e) of claim 21.

* * * * *